United States Patent
Lewis et al.

(10) Patent No.: US 7,705,198 B2
(45) Date of Patent: Apr. 27, 2010

(54) KSR2 KNOCKOUT MICE AND METHODS OF USE THEREOF

(75) Inventors: Robert E. Lewis, Omaha, NE (US);
Diane Costanzo, Omaha, NE (US);
Aimee Schreiner, Papillion, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 0 days.

(21) Appl. No.: 11/431,285

(22) Filed: May 10, 2006

(65) Prior Publication Data
US 2007/0266452 A1     Nov. 15, 2007

(51) Int. Cl.
*A01K 67/027* (2006.01)
*A61K 49/00* (2006.01)
*C12N 5/00* (2006.01)

(52) U.S. Cl. .......................... 800/18; 424/9.2; 435/375

(58) Field of Classification Search .................. 800/18; 424/9.2; 435/375
See application file for complete search history.

(56) References Cited

U.S. PATENT DOCUMENTS

| | | | |
|---|---|---|---|
| 6,891,081 B1 | 5/2005 | Stern et al. |
| 6,897,352 B2 | 5/2005 | Verma et al. |
| 6,909,030 B2 | 6/2005 | Melmed et al. |
| 6,921,845 B1 | 7/2005 | Amson et al. |
| 2005/0125852 A1 | 6/2005 | Caenepeel et al. |

OTHER PUBLICATIONS

Doetschman, Lab. Animal Sci., vol. 49 (2), 137-143; 1999.*
Wolfer et al Trends in Neuroscience, 25 (7): 336-340; 2002.*
Schoonjans et al. Stem Cells 21:90-97; 2003.*
Kortum et al. Mol. Cell Biiol. 25, 7592-7604; 2005.*
Cacace, A.M., et al.,"Identification of constitutive and Ras-inducible phosphorylation sites of KSR: implications for 14-3-3 binding, mitogen-activated protein kinase binding, and KSR overexpression," Mol. Cell. Biol., 19(1):229-240, (Jan. 1999).
Channavajhala, P.L., et al., "Identification of a novel human kinase supporter of Ras (hKSR-2) that functions as a negative regulator of Cot (Tp12) signaling," J. Biol. Chem., 278(47):47089-47097, (Nov. 21, 2003).
Clement, K., et al., "Genetics of human obesity," Symposium on "Genes, behaviour and environment," Proc. Nutr. Soc., 64:133-142, (2005).
Douziech, M., et al., "A KSR/CNK complex mediated by HYP, a novel SAM domain-containing protein, regulates RAS-dependent RAF activation in Drosophila," Genes & Dev., 20:807-819, (2006), 1 cover sheet, sheet C-1, and 2 sheets "Contents."
Farooqi, I.S., et al., "Monogenic obesity in humans," Annu. Rev. Med., 56:443-58, (2005).
Haslam, D.W., et al., "Obesity," Lancet, 366:1197-1209, (2005).
Kornfeld, K., et al., "The ksr-1 gene encodes a novel protein kinase involved in Ras-mediated singaling in C. elegans," Cell, 83:903-913, (Dec. 15, 1995).

Kortum, R.L., et al., "The molecular scaffold KSR1 regulates the proliferative and oncogenic potential of cells," Mol. Cell. Biol., 24(10):4407-4416, (May 2004).
Kortum, R.L., et al., "The molecular scaffold kinase suppressor of Ras 1 is a modifier of RasV12-induced and replicative senescence," Mol. Cell. Biol., 26(6):2202-2214, (Mar. 2006).
Kortum, R.L., et al., "The molecular scaffold kinase suppressor of Ras 1 (KSR1) regulates adipogenesis," Mol. Cell. Biol., 25(17):7592-7604, (Sep. 2005).
Kristensen, P., et al., "Hypothalamic CART is a new anorectic peptide regulated by leptin," Nature, 393:72-76, (May 7, 1998).
Lazar, M.A., et al., "How obesity casuses diabetes: not a tall tale," Science, 307:373-375 (2005) and cover sheet.
Lelay, S., et al., "Cholesterol, a cell size-dependent signal that regulates glucose metabolism and gene expression in adipocytes," J. Biol. Chem., 276(20):16904-16910, (May 18, 2001).
Lowell, B.B., et al., "Towards a molecular understanding of adaptive thermogenesis," Nature, 404:652-660, (Apr. 6, 2000).
Lozano, J., et al., "Deficiency of kinase suppressor of Ras1 prevents oncogenic Ras signaling in mice," Can. Res., 63:4232-4238, (Jul. 15, 2003).
Mousel, M.R., et al., "Locomotor activity, core body temperature, and circadian rhythms in mice selected for high or low heat loss," J. Anim. Sci., 79:861-868, (2001).
Muller, J., et al., "Identification of B-KSR1, a novel brain-specific isoform of KSR1 that functions in neuronal signaling," Mol. Cell. Biol., 20(15):5529-5539, (Aug. 2000).
Muller, J., et al., "C-TAK1 regulates Ras signaling by phosphorylating the MAPK scaffod, KSR1," Mol. Cell, 8:983-993, (Nov. 2001).
Nguyen, A., et al., "Kinase suppressor of Ras (KSR) is a scaffold which facilitates mitogen-activated protein kinase activation in vivo," Mol. Cell. Biol., 22(9):3035-3045, (May 2002).
Ohmachi, M., et al., "C. elegans ksr-1 and ksr-2 have both unique and redundant functions and are required for MPK-1 ERK phosphorylation," Curr. Biol., 12:427-433, (Mar. 5, 2002).
Schwartz, M.W., et al., "Central nervous system control of food intake," Nature, 404(6778):661-671, (Apr. 6, 2000).
Sundaram, M., et al., "The C. elegans ksr-1 gene encodes a novel Raf-related kinase involved in Ras-mediated signal transduction," Cell, 83:889-901, (Dec. 15, 1995).
Therrien, M., et al., "KSR, a novel protein kinase required for RAS signal transduction," Cell, 83:879-888, (Dec. 15, 1995).
Therrien, M., et al., "KSR modulates signal propagation within the MAPK cascade," Genes & Dev., 10:2684-2695, (1996) and 1 cover sheet.

(Continued)

*Primary Examiner*—Fereydoun G Sajjadi
(74) *Attorney, Agent, or Firm*—Dann, Dorfman, Herrell & Skillman; Kathleen D. Rigaut

(57) ABSTRACT

A transgenic non-human animal with a homologous disruption of the KSR-2 gene is disclosed. Methods for using transgenic mice so generated to screen for agents that effect cellular metabolism are also provided.

12 Claims, 25 Drawing Sheets

OTHER PUBLICATIONS

Bray, G.A., et al., "Hypothalamic and genetic obesity in experimental animals: an autonomic and endocrine hypothesis," Physiol. Rev., 59(3):719-809, (Jul. 1979).

Lewis, R., "A model system for analysis of scaffold function on RAF/MEK/ERK signaling," presented on Jul. 27, 2005.

Halaas, J.L. et al., "Weight-reducing effects of the plasma protein encoded by the obese gene," Science, 269:543-6 (1995).

Olefsky, J.M., "Mechanisms of decreased insulin responsiveness of large adipocytes," Endocrinology, 100(4):1169-77, (1977).

Ravussin, E. et al., "Reduced rate of energy expenditure as a risk factor for body-weight gain," N. Engl. J. Med., 318 (8):467-72, (Feb. 25, 1988).

* cited by examiner

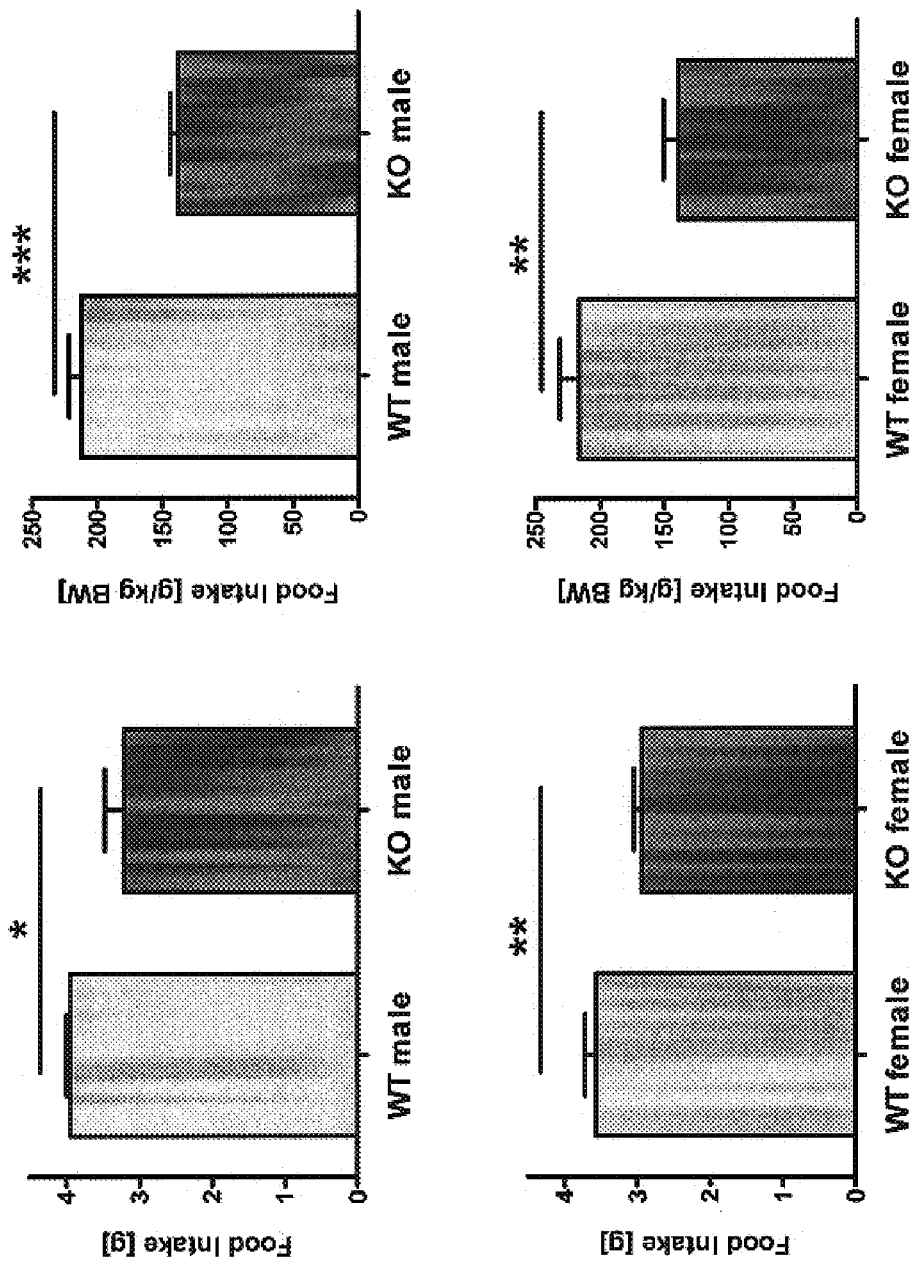

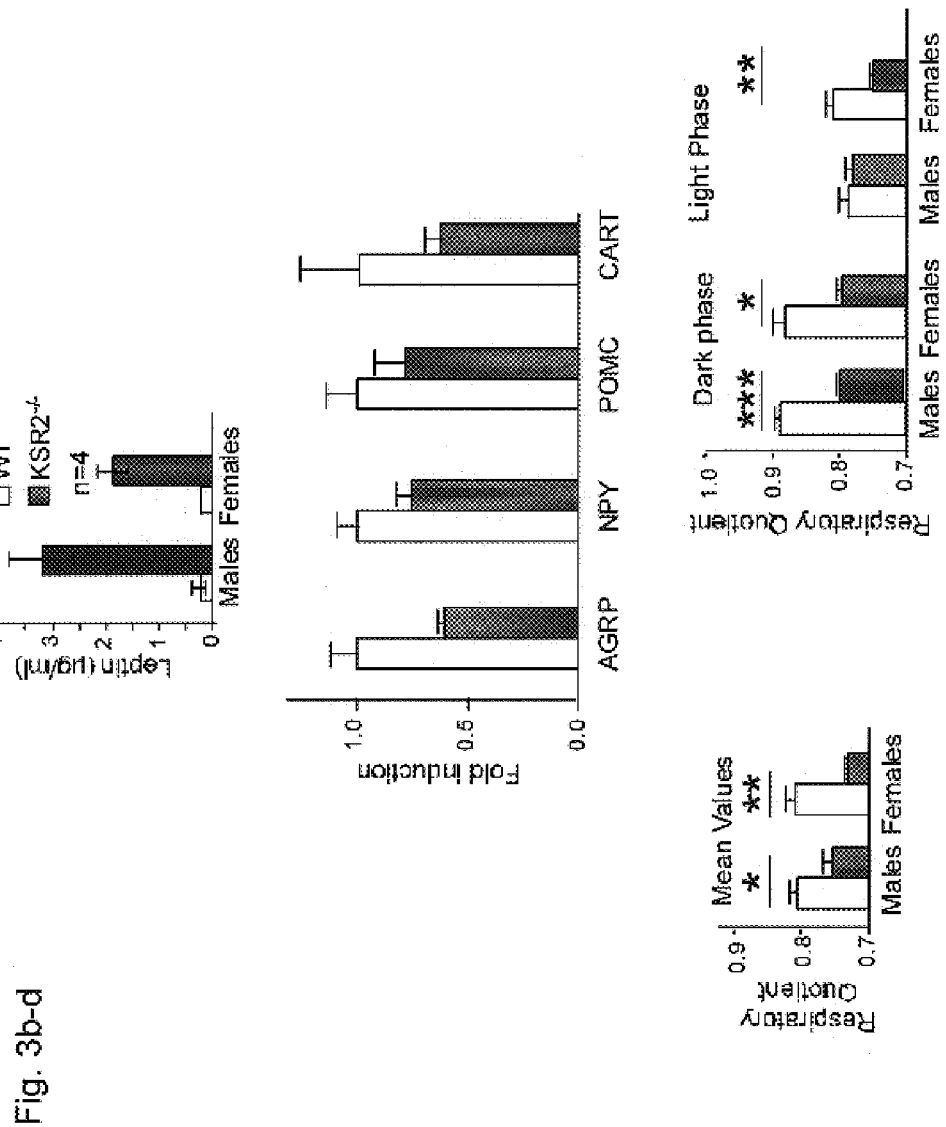
Fig. 3b-d

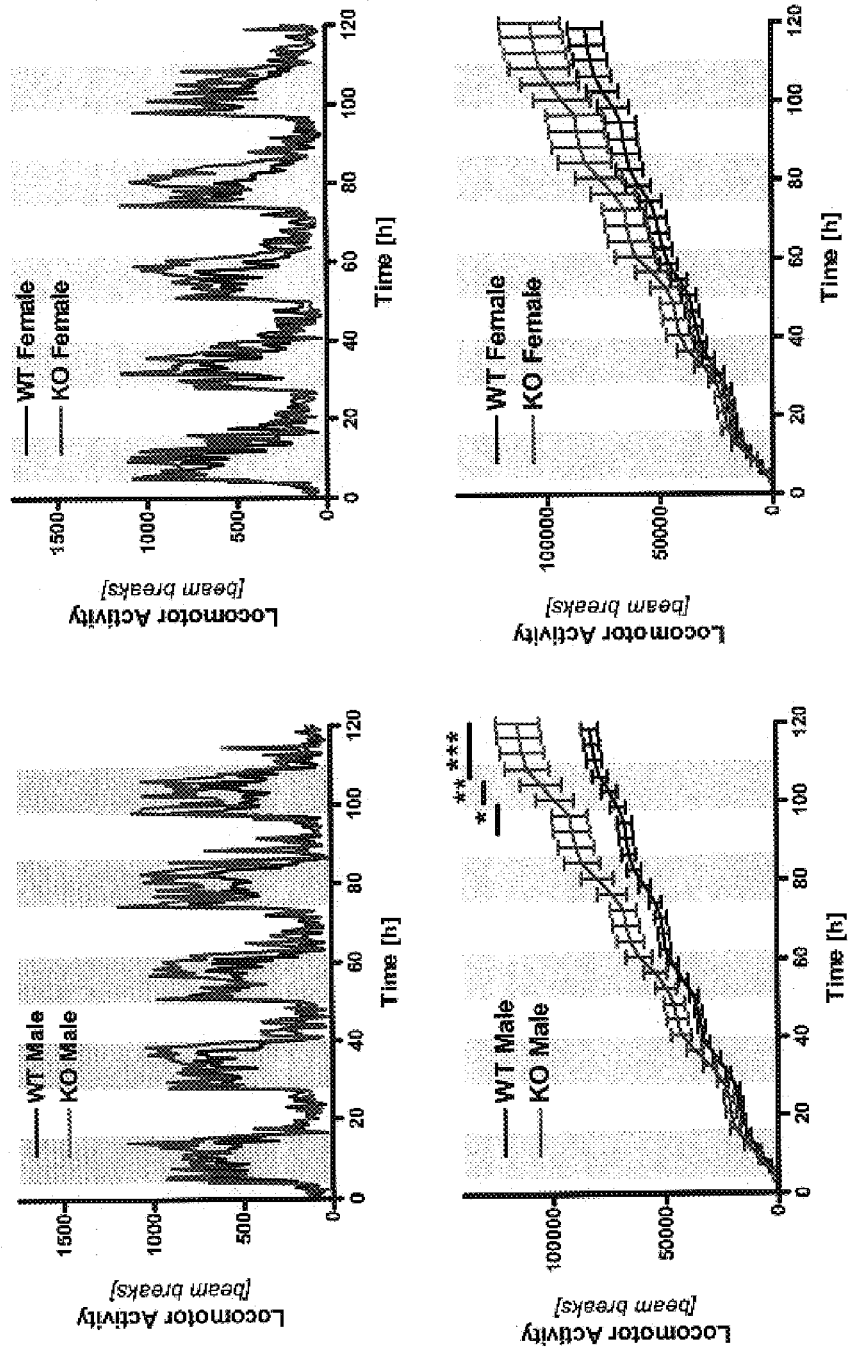

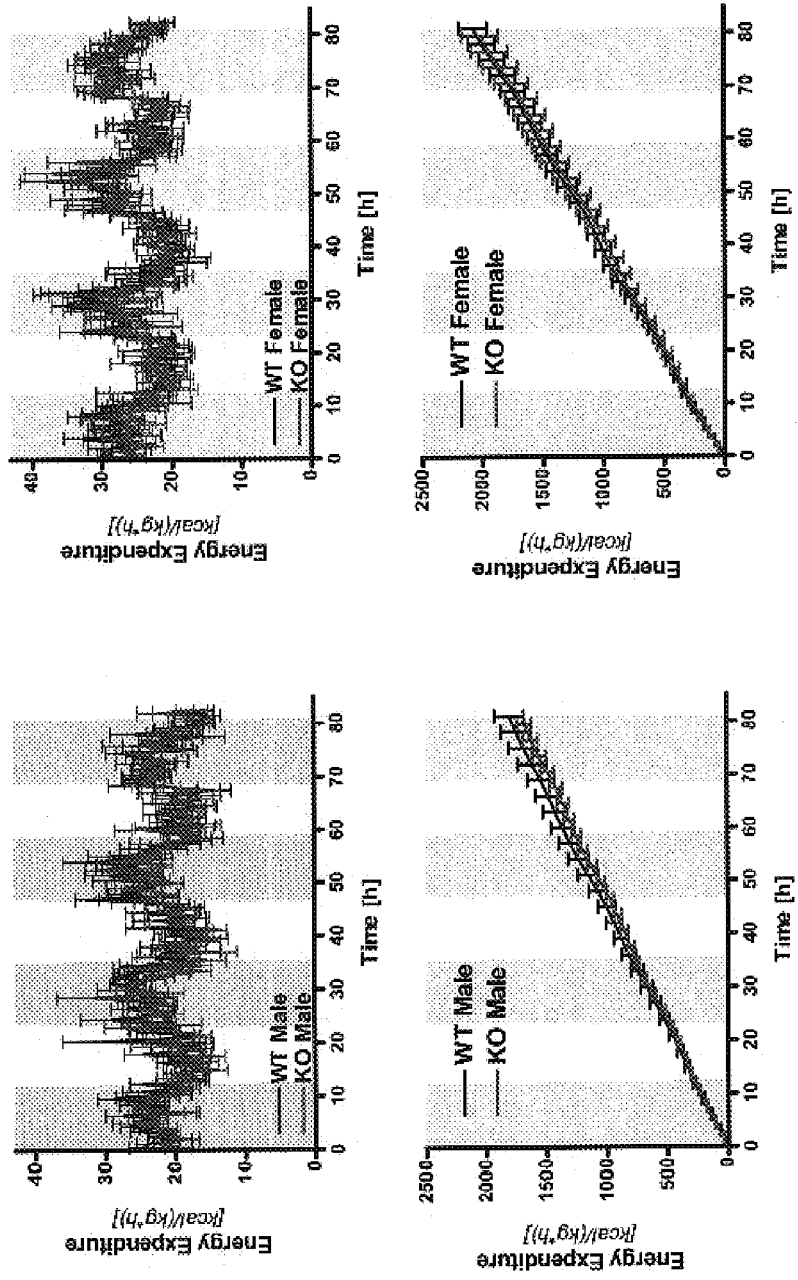

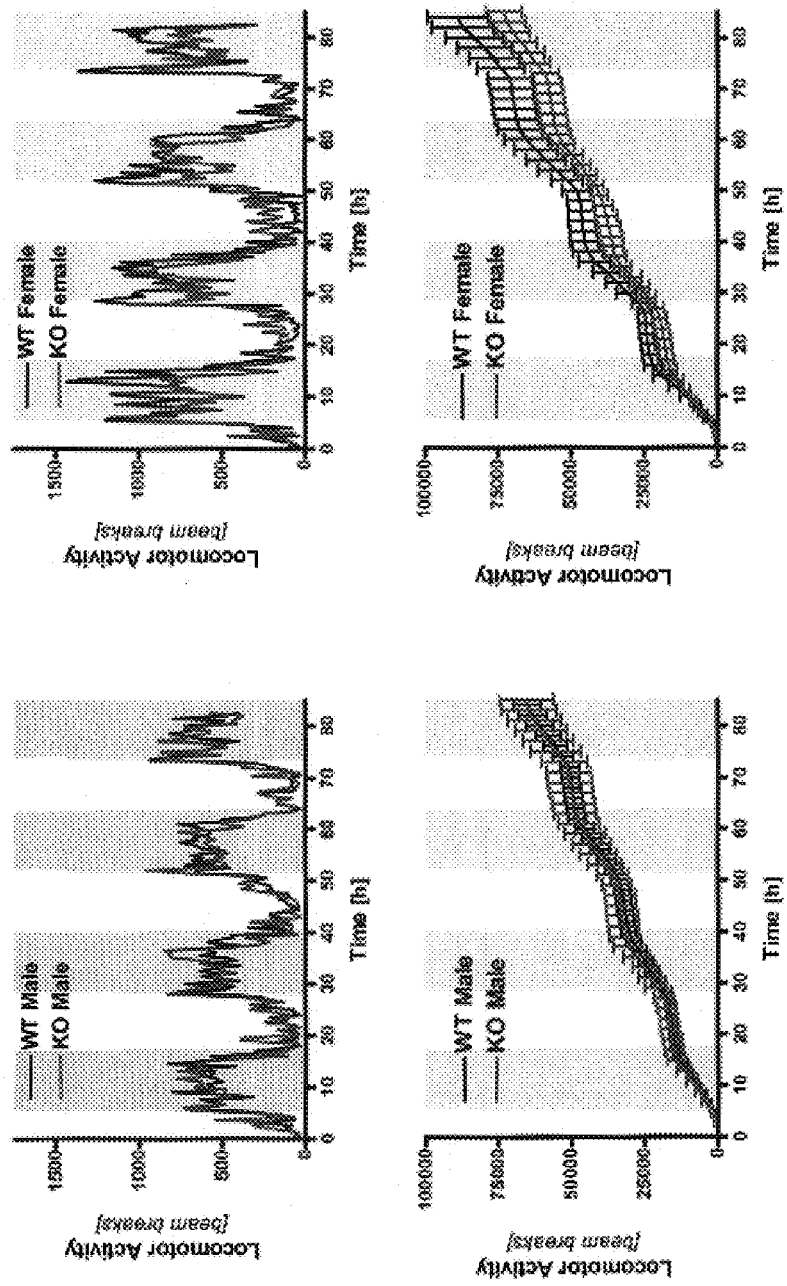

KSR2 KNOCKOUT MICE AND METHODS OF USE THEREOF

Pursuant to 35 U.S.C. §202(c) it is acknowledged that the U.S. Government has certain rights in the invention described herein, which was made in part with funds from the National Institutes of Health, Grant Number, DK52809.

FIELD OF THE INVENTION

This invention relates the fields of recombinant DNA technology, transgenic animals and metabolic regulation. More specifically, a transgenic nonhuman animal is provided wherein the KSR2 gene has been altered. Methods of using such animals to assess KRS2's role in the modulation of energy expenditure, weight gain and diabetes susceptibility are also provided.

BACKGROUND OF THE INVENTION

Several publications and patent documents are cited in this application in order to more fully describe the state of the art to which this invention pertains. The disclosure of each of these citations is incorporated herein by reference.

The worldwide epidemic in obesity has brought with it dramatic increases in the prevalence of co-morbid, chronic conditions including insulin resistance, type 2 diabetes, the metabolic syndrome, and atherosclerosis. The rapid rise in these major public health problems underscores a growing need to understand the physiological and pathological bases of feeding and obesity, and the pathophysiological links between obesity and these associated morbidities.

Kinase Suppressor of Ras (KSR) is a conserved protein that positively regulates Ras signaling and functions as a scaffold for Raf, MEK, and ERK. However, the precise role of KSR is not well understood, and some observations have suggested that KSR might act in a parallel pathway. In C. elegans, ksr-1 is only required for a specific Ras-mediated process (sex myoblast migration) and is a nonessential positive regulator of other Ras-mediated developmental events. A second C. elegans ksr gene, ksr-2 has also been identified, which is required for Ras-mediated signaling during germline meiotic progression and functions redundantly with ksr-1 during development. Thus, while the ksr-1 and ksr-2 genes are individually required only for specific Ras-dependent processes, together these two genes appear necessary for most aspects of Ras-mediated signaling. The finding that ksr-2; ksr-1 double mutants have strong ras-like phenotypes and severely reduced or absent levels of diphosphorylated MPK-1 ERK strongly supports models where KSR acts to promote the activation or maintenance of the Raf/MEK/ERK kinase cascade.

It is an object of the invention to provide a whole animal model for studying these interactions, thereby identifying agents which modulate aberrant processes associated with abnormal KSR2 function.

SUMMARY OF THE INVENTION

In accordance with the present invention, a transgenic mouse comprising a homozygous disruption of the KSR-2 gene is provided. The mouse of the invention does not express KSR-2 protein and exhibits a phenotype comprising increased obesity and reduced energy expenditure. Such mice may be used to advantage to identify agents which modulate energy expenditure, weight gain and diabetes susceptibility. In another embodiment, the KSR-2 knockout mouse of the invention further comprises a homologous disruption of KSR-1. Also encompassed by the invention are cells isolated from such animals for use in screening methods to identify therapeutic agents which modulate KSR-2 and/or KSR-1 function.

In a preferred embodiment of the invention, a method for screening an agent for the ability to modulate energy expenditure in a whole animal model is disclosed. An exemplary method entails administering the agent to the transgenic mice described above, measuring at least one energy expenditure parameter in the treated mouse and comparing the measurement obtained to that of a transgenic littermate not administered the agent, thereby identifying agents which modulate energy expenditure in the treated mouse relative to the control, non-treated mouse. Preferably, the at least one energy expenditure parameter is selected from the group consisting of weight, body fat composition, adipose cell mass, adipose cell size, food intake, respiratory quotient, energy expenditure, glucose tolerance, locomoter activity and rectal temperature. A further aspect of the method invention entails isolating cells from said mouse and exposing said cells to said agent in vitro.

In yet another aspect, progeny animals obtained from the KSR-2 knockout mice are within the scope of the present invention.

BRIEF DESCRIPTION OF THE DRAWINGS

FIG. 9. FIG. 9D is a series of graphs showing energy expenditure in male and female wild type and knock out mice. FIG. 9F is a series of graphs measuring locomoter activity in male and female wild type and knock out mice.

DETAILED DESCRIPTION OF THE INVENTION

Figure 1A:
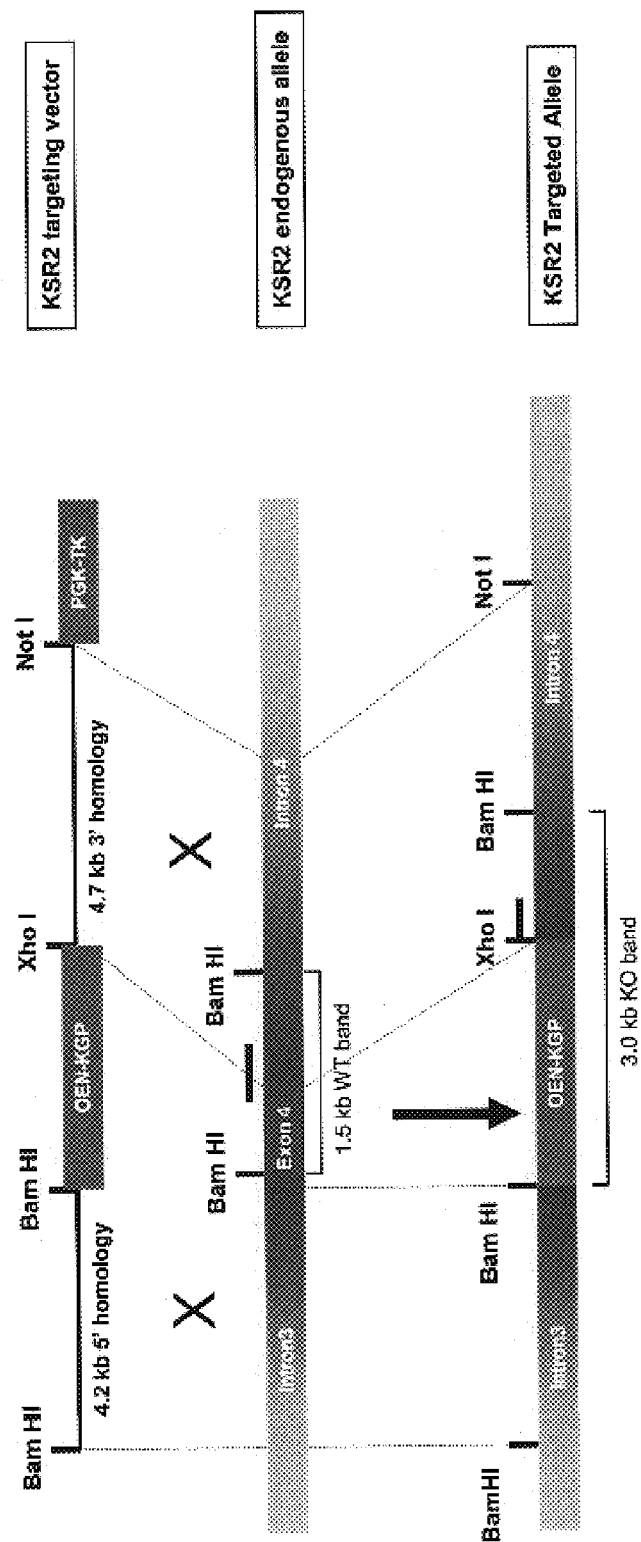
FIG. 1. Targeted disruption of ksr2 and its effect growth and development. a, Strategy for targeted disruption of ksr2. The targeting vector used to generate the ksr2 null allele eliminates most of exon 4, and inserts a stop codon. b, Genotype analysis of DNA from mice showing targeting of the ksr2 locus. c, Southern analysis of the null (−/−), heterozygous (+/−) and wild-type (+/+) alleles. d, Western analysis of ksr2$^{-/-}$ (−/−), wild-type (+/+) brain and ectopic KSR2 expressed in HEK 293T cells (C), using an antibody directed against amino acids 154-272 of mouse KSR2. e, Null (−/−), heterozygous (+/−) and wild-type (+/+) mice at day E18.5 (left panel), and eight days (middle panel) and 24 weeks (right panel) of age. f, Growth patterns male and female null (triangles), heterozygous (circles) and wild-type (squares) mice.

Obesity is a major health problem in the western world with increasing prevalence in developing nations[1]. Obesity is typically a consequence of complex inherited traits and environmental impact[2], though characterization of unique forms of monogenetic obesity has provided valuable insight into the molecular mechanisms that underlie the complex control of energy balance in humans[3]. Kinase Suppressor of Ras 1 and 2 (KSR1 and KSR 2) potently regulate the MAP kinases ERK1/2 to affect multiple cell fates[4-9].

Their effects on ERK can be ascribed to their ability to function as molecular scaffolds that facilitate signal transduction between upstream kinases and ERK[5-7,10], though they may also dynamically regulate pathway output[6,11]. Disruption of KSR1 impairs growth factor-regulated ERK activation and causes resistance to Ras-mediated tumorigenesis in vivo and in vitro[7,10,12] KSR1 disruption also impairs adipocyte proliferation in vivo and differentization in vitro[5].

A transgenic animal carrying a "knock out" of KSR-2 is useful for the establishment of a nonhuman model for diseases involving KSR-2 regulation. In accordance with the present invention, mice comprising a disruption of KSR2 exhibit spontaneous obesity. Despite their increased adiposity ksr2$^{-/-}$ mice eat less that wild-type mice, are more active than wild-type mice, preferentially metabolize fat, but expend less energy than wild-type mice. Hyperinsulinemic euglycemic clamp studies reveal that ksr2$^{-/-}$ mice are profoundly insulin resistant. Similar to obesity-prone populations of southwestern native Americans[13], these data demonstrate that ksr2$^{-/-}$ mice are energy efficient and reveal a novel role for KSR2 and MAP kinase signaling in the regulation of energy homeostasis and the control of glucose metabolism.

The phrase "energy parameter" as used herein refers to a parameter selected from the group consisting of weight, body fat composition, adipose cell mass, adipose cell size, food intake, respiratory quotient, energy expenditure, glucose tolerance, locomoter activity and body temperature.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA.

The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered KSR-2 gene generally should not fully encode the same KSR-2 protein native to the host animal and its expression product should be altered to a minor or great degree, or absent altogether. However, it is conceivable that a more modestly modified KSR-2 gene will fall within the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated KSR-2 genes to selectively inactivate the wild-type gene in totipotent ES cells (such as those described above) and then generate transgenic mice. The use of gene-targeted ES cells in the generation of gene-targeted transgenic mice has been previously described.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the fraction of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Such mice may be used to advantage to identify agents which augment, inhibit or modify the activities of KSR-2. For example, disruption of KSR-2 causes spontaneous obesity. Accordingly, therapeutic agents for the treatment or prevention of obesity may be screened in studies using the KSR-2 knock out mice of the invention. For example, KSR-2 knockout mice may be treated with a test compound that modulates the regulation of energy homeostasis and the control of glucose metabolism. Such assays will not only facilitate the identification of agents which regulate metabolic rates, they should also be illustrative of the underlying biochemical mechanisms which underlie the development of obesity and/or type II diabetes.

In another embodiment of the invention, KSR-2 knockout mice can be used to produce an array of monoclonal antibodies specific for KSR-2.

The example set forth below is provided to illustrate certain embodiments of the invention. It is not intended to limit the invention in any way.

Example I

KSR-2 KO Mice and Analysis of Resulting Phenotype

The following methods are provided to facilitate the practice of the present invention.

Mice

Standard gene-targeting techniques and homologous recombination were used to generate $KSR^{-/-}$ mutant mice. The Institutional Animal Care and Use Committee (University of Nebraska Medical Center, Omaha, Nebr.) approved all studies. Animals were maintained on a 12-hour light/dark-schedule (light on at 0600) and had free access to laboratory chow and water.

Immunoblots

Post-nuclear membranes prepared from brain tissue were immunoblotted for KSR2. Tissue was prepared by homogenization using a Polytron at medium setting in 50 mM Tris (pH 7.5), 150 mM NaCl, 1 mM EDTA, 1% Triton X-100, 1 mM $Na_3VO_4$, 1 mM NaF and protease inhibitor cocktail (Sigma). Tissue and cell debris were removed by centrifugation. Protein concentration was determined with the BCA assay (Pierce). The resulting supernatant was used for immunoblotting.

Body Composition and Adipocyte Size

Body composition was determined by $^1H$ magnetic resonance spectroscopy (Echo Medical Systems). Total adipose tissue from each depot was excised and the wet weight was determined. Abdominal subcutaneous adipose tissue was fixed in Bouins fixative, sectioned in a microtome and stained with hematoxylin and eosin. Adipocyte cross-sectional area was determined from photomicrographs of epididymal fat pads using IPLab software (Scanalytics Inc., Fairfax, Va.)[5].

Metabolic Phenotype Analysis

Food intake was measured daily over five consecutive days in freely feeding mice. Locomotor activity was measured using automated video monitoring system HomeCageScan (Clever Systems). Total energy expenditure and relative rates of carbohydrate versus fat oxidation were determined by indirect calorimetry using a Customized Indirect Calorimetry system (TSE).

Metabolite Assays

Blood glucose was measured with an Ascensia Glucometer Elite (Fisher Scientific). Plasma insulin was measured with the Rat/Mouse Insulin Elisa Kit (ChrystalChem, Chicago, Ill.) using rat standards. Serum free fatty acids were measured using the NEFA-C kit (Wako Chemicals GMBH, Neuss, Germany) with oleic acid as the standard. Plasma triglycerides and glycerol were measured using the GPO-Trinder colorimetric assay kit (Sigma). Plasma leptin was measured using the Rat Leptin RIA kit (Linco Research, St Louis, Mo.).

Glucose and Insulin Tolerance Tests

Glucose tolerance tests were performed with an intraperitoneal injection of 2 mg/kg glucose in awake mice after a 10 h fast. Blood glucose was sampled from the tail vein at intervals from 0-120 min. Insulin tolerance tests were performed with an intraperitoneal injection of 0.75 U/kg insulin in awake mice after a 4 h fast. In both tests, blood glucose was sampled from the tail vein at intervals from 0-120 min.

Hyperinsulinemic-Euglycemic Clamps to Assess Insulin Action In Vivo

Following an overnight fast (~15 hour), a 2-hour hyperinsulinemic-euglycemic clamp was conducted in awake ksr2$^{-/-}$ mice and wild-type littermates (n=8~11) with a continuous infusion of human regular insulin (Humulin; Eli Lilly, Indianapolis, Ind.) at a rate of 15 pmol/kg/min to raise plasma insulin within a physiological range (~300 pM). Blood samples (20 µl) were collected at 20 min intervals for the immediate measurement of plasma glucose concentration, and 20% glucose was infused at variable rates to maintain euglycemia. Basal and insulin-stimulated whole body glucose turnover was estimated with a continuous infusion of [3-$^3$H]glucose (PerkinElmer Life and Analytical Sciences, Boston, Mass.) for 2 hours prior to the clamps (0.05 µCi/min) and throughout the clamps (0.1 µCi/min), respectively. To estimate insulin-stimulated glucose uptake in individual tissues, 2-deoxy-D-[1-$^{14}$C]glucose (2-[$^{14}$C]DG) was administered as a bolus (10 µCi) at 75 min after the start of clamps. Blood samples were taken before, during, and at the end of clamps for the measurement of plasma [$^3$H]glucose, $^3$H$_2$O, 2-[$^{14}$C]DG concentrations, and/or insulin concentrations. At the end of clamps, mice were euthanized, and tissues were taken for biochemical analysis.

Plasma concentrations of [3-$^3$H]glucose, 2-[$^{14}$C]DG, and $^3$H$_2$O were determined following deproteinization of plasma samples as previously described. Intracellular levels of 2-[$^{14}$C]DG-6-phosphate (2-[$^{14}$C]DG-6-P) in individual organs (i.e., skeletal muscle, white and brown adipose tissue) were determined using an ion-exchange column as previously described. Rates of basal HGP and insulin-stimulated whole body glucose turnover were determined as the ratio of the [$^3$H]glucose infusion rate (disintegrations per minute; dpm/min) to the specific activity of plasma glucose (dpm/µmol) at the end of basal period and during the final 30 min of clamp, respectively. Insulin-stimulated rate of HGP during clamp was determined by subtracting the glucose infusion rate from whole body glucose turnover. Whole body glycolysis was calculated from the rate of increase in plasma $^3$H$_2$O concentration, determined by linear regression of the measurements at 80, 90, 100, 110, and 120 min of clamps. Whole body glycogen plus lipid synthesis from glucose was estimated by subtracting whole body glycolysis from whole body glucose turnover. Since 2-deoxyglucose is a glucose analog that is phosphorylated but not further metabolized, insulin-stimulated glucose uptake in individual tissues can be estimated by determining the tissue (i.e., skeletal muscle, adipose tissue) content of 2-[$^{14}$C]DG-6-P. Based on this, glucose uptake in individual tissues was calculated from plasma 2-[$^{14}$C]DG profile and tissue 2-[$^{14}$C]DG-6-P content.

Statistical Analysis

Data are expressed as mean±s.e.m. Differences between two groups were assessed using the unpaired two-tailed t-test and among more than two groups by analysis of variance (ANOVA).

Results

Figure 1B:
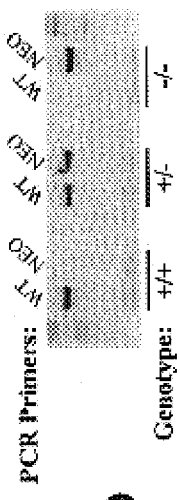
Figure 1C:
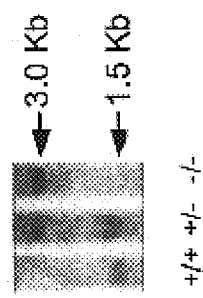
Figure 1D:
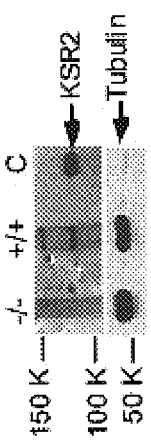
Figure 1E:
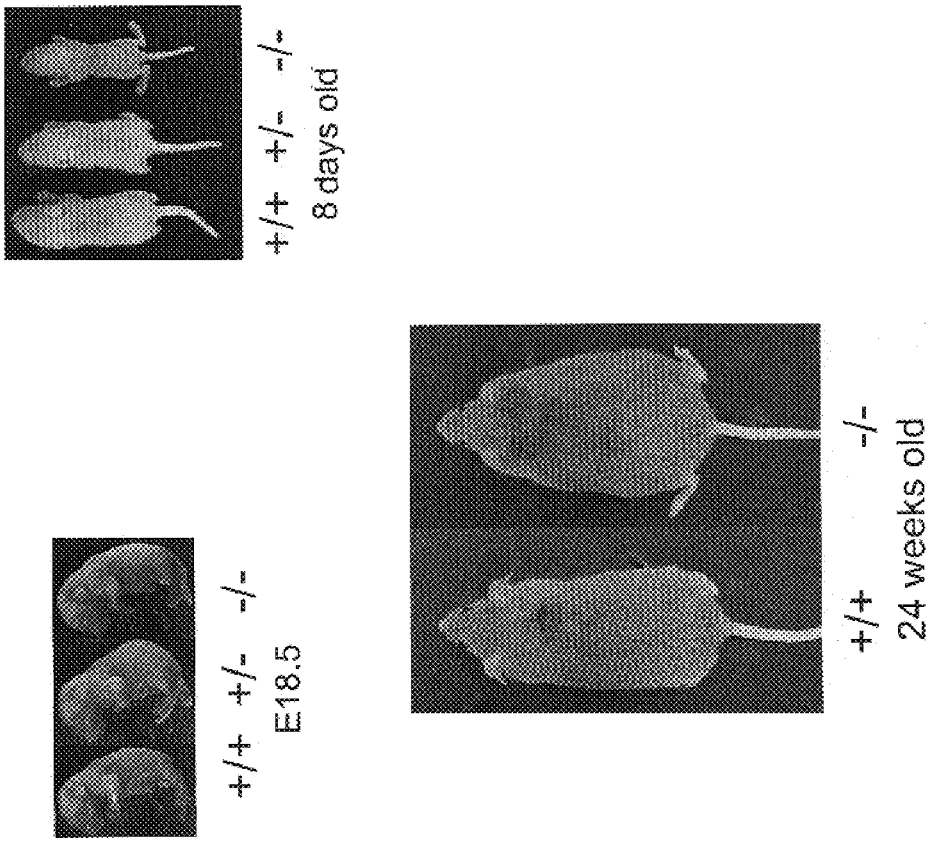
Figure 1F:
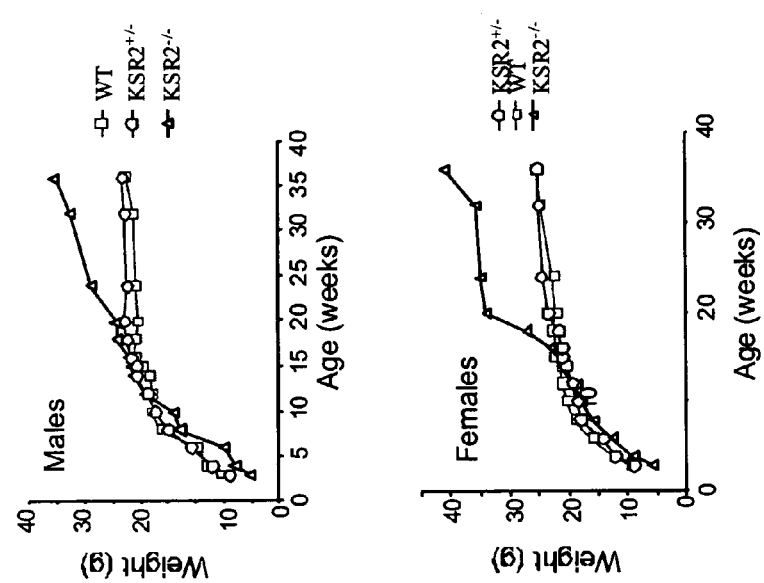
Figure 6:
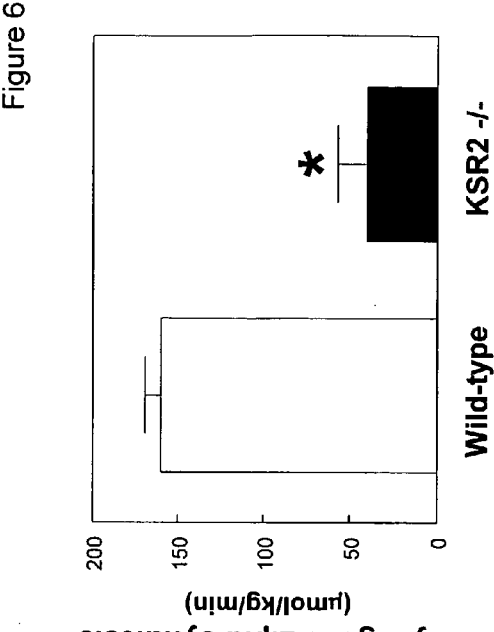
FIG. 6. Insulin-stimulated whole body glucose metabolism in vivo in ksr2$^{-/-}$ mice. A. Insulin-stimulated whole body glucose turnover. B. Insulin-stimulated whole body glycogen plus lipid synthesis. C. Insulin-stimulated whole body glycolysis. Values are means±S.E. for 8~11 experiments. *P<0.05 vs. wild-type mice.
Figure 6:
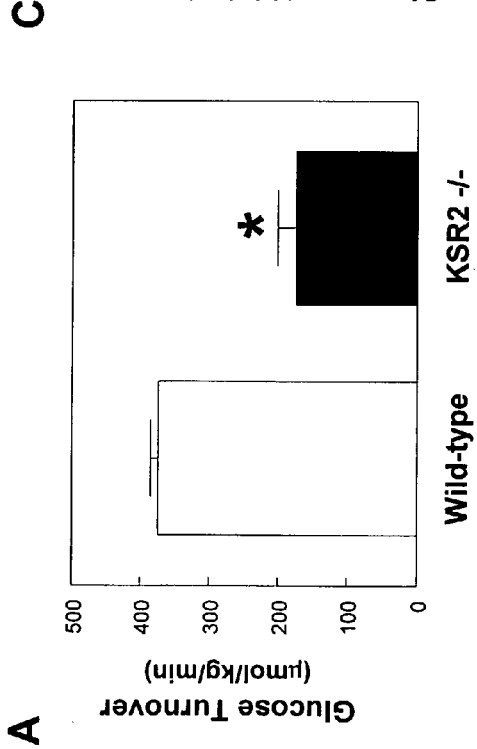
Figure 6:
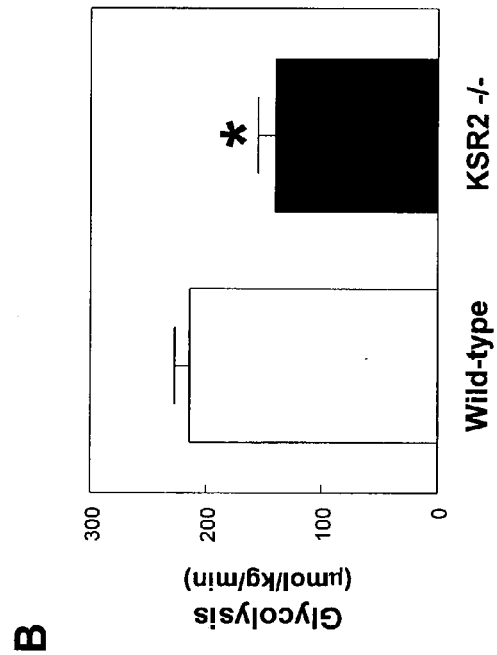

To disrupt the ksr2 ORF, exon 4 was replaced with a neo$^r$ cassette in DBA1/LacJ ES cells by homologous recombination (FIG. 1a). The 5' homology arm of the targeting vector included the first 25 bases of exon 4 and a stop codon to prevent exon skipping and the production of an aberrant endogenous Ksr2 protein. The targeted deletion also removed the splice junction between exon 4 and intron 4. The ksr2-null allele was transmitted through the germ line, and heterozygous intercrosses yielded all three genotypes (FIG. 1b) in a ratio close to the expected Mendelian distribution (relative ratios ksr2$^{+/+}$1, ksr2$^{+/-}$2.25, ksr2$^{-/-}$0.91; n=441). Polymerase chain reaction (PCR) with 5'-oligomers targeted to the deleted region or to the neo gene was used to confirm that the mutant mice had a disrupted ksr2 locus. A ksr2-specific band was detected in genomic DNA from ksr2$^{+/+}$ and ksr2$^{+/-}$, but not ksr2$^{-/-}$ mice. Similarly, a neo-specific band was detected in ksr2$^{-/-}$ and ksr2$^{+/-}$, but not ksr2$^{+/+}$ mice (FIG. 1c). Western blot analysis with antibodies directed against a GST-Ksr2 fusion protein detected Ksr2 on western blots of whole brain lysates from ksr2$^{+/+}$ but not ksr2$^{-/-}$ mice (FIG. 1d). The immunoreactive band detected in ksr2$^{+/+}$ mice had an electrophoretic mobility identical to mouse KSR2 transiently expressed in 293T HEK cells from a cDNA cloned from mouse brain (FIG. 6). A higher molecular weight band of immunoreactivity was also detected brain lysates from ksr2$^{+/+}$ mice. This band may represent a spliced form of KSR2 analogous to the alternatively spliced form of KSR1 also detected in mouse brain[9].

ksr2$^{-/-}$ mice were identical in size and weight to ksr2$^{+/+}$ and ksr2$^{+/-}$ mice during development in utero and at birth (FIG. 1e, left panel). However, while nursing, ksr2$^{-/-}$ grew at approximately 50% the rate observed in ksr2$^{+/+}$ and ksr2$^{+/-}$ mice (FIG. 1e, right panel). Thirty two percent of ksr2$^{-/-}$ mice (31 of 98) failed to survive until weaning. Premature death was not due to the failure of ksr2$^{-/-}$ pups to nurse properly as all mice had milk in their stomachs upon necropsy. The addition of foster mothers did not improve survival. Furthermore, nutrient absorption was identical in ksr2$^{+/+}$ and ksr2$^{-/-}$ mice (not shown). The growth rate of surviving ksr2$^{-/-}$ mice was measured. ksr2$^{-/-}$ mice attained weights similar to wild-type and ksr2$^{+/-}$ mice within 6-10 weeks after birth (FIG. 1f). At 20-24 weeks of age, ksr2$^{-/-}$ mice exceeded the weight of their ksr2$^{+/+}$ and ksr2$^{+/-}$ littermates and became obese (FIG. 1e, lower panel).

Figure 2A:
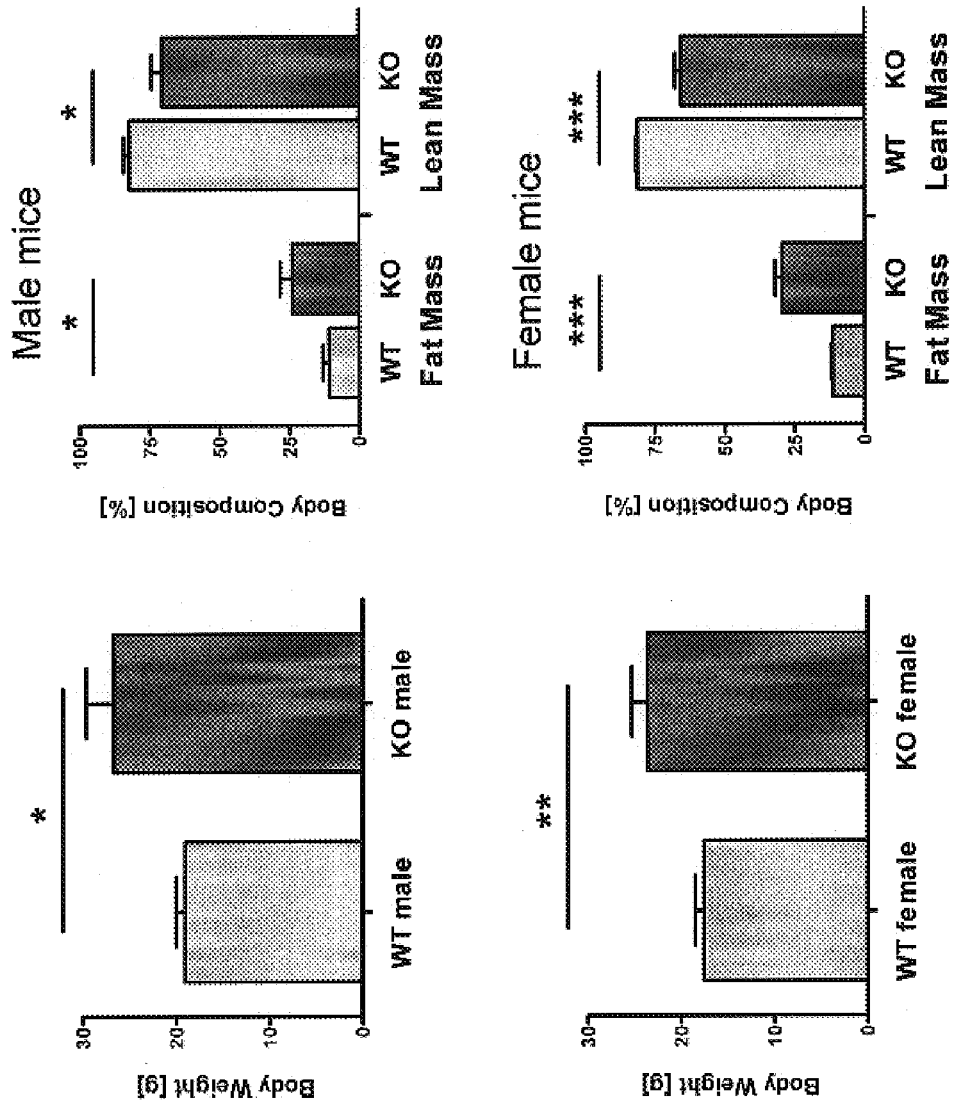
FIG. 2. Altered adipocyte morphology and function in ksr2$^{-/-}$ mice. a, Body weight and body composition of wild-type (WT) and ksr2$^{-/-}$ mice. b, Wet weight of visceral (VISC), inguinal (ING), subcutaneous (SUB) and brown (BAT) adipose depots in wild-type and ksr2$^{-/-}$ mice. c, Adipocyte cross-sectional area in wild-type and ksr2$^{-/-}$ mice. Hematoxylin and eosin staining of histological sections from subcutaneous adipose tissue are shown. d, Hematoxylin and eosin staining of histological sections from brown adipose tissue from wild-type and ksr2$^{-/-}$ mice. e, rectal temperature in wild-type (dark bars) and ksr2$^{-/-}$ mice (white bars) during active (9 pm) and quiet (1 pm) cycles. f, cold tolerance in wild-type (squares) and ksr2$^{-1}$ female mice (circles). Mice were kept at 4° C. for 2 h and rectal temperature was measured at 30 min intervals.
Figure 2B:
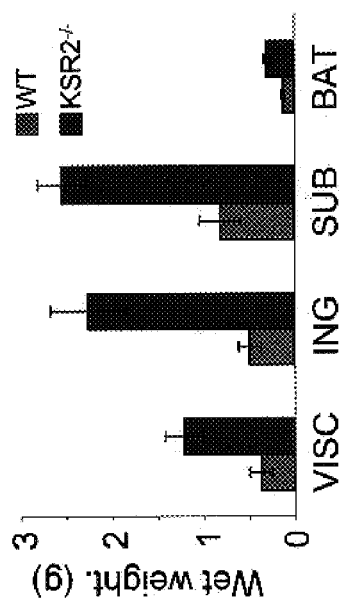
Figure 2C:
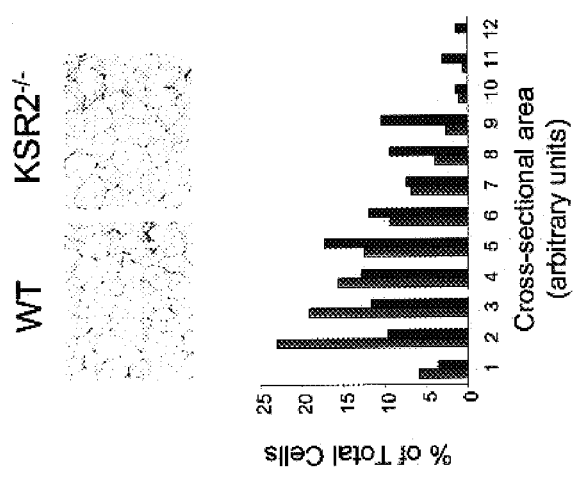
Figure 2D:
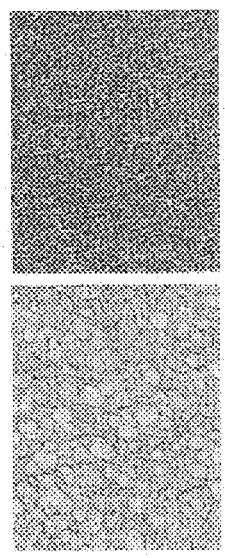
Figure 2E:
Figure 2F:
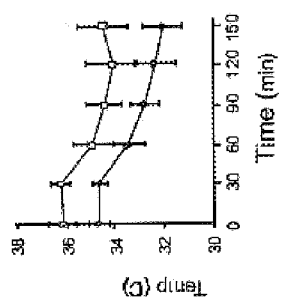

Disruption of ksr2$^{-/-}$ caused a doubling in fat mass and a 15% decrease in lean mass (FIG. 2a). All adipose depots from ksr2$^{-/-}$ mice were increased in mass relative to ksr2$^{+/+}$ mice (FIG. 2b). Histological analysis demonstrated that the cross-sectional area of white adipose tissue in ksr2$^{-/-}$ mice was increased in size relative to ksr2$^{+/+}$ mice (FIG. 2c). Large lipid vesicles were detected in the brown adipose tissue (BAT) of ksr2$^{-/-}$ mice that were not present in BAT from ksr2$^{+/+}$ mice (FIG. 2d). BAT is the major site of adaptive thermogenesis in rodents[14]. Adaptive thermogenesis protects mammals from cold exposure and regulates energy balance when diet is altered[14]. To assess whether this lipid accumulation was reflected in a reduced heat generation, the rectal temperature of wild type and ksr2-mice was compared during active and resting periods. In comparison to ksr2$^{+/+}$ mice, the rectal temperature of ksr2$^{-/-}$ mice was lowered by as much as 1.5° C. (FIG. 2e). To place this temperature difference in perspective, selective breeding for heat loss in mice over 20 generations resulted in obese mice with a 0.5° C. decrease in body temperatures[15]. The reduced rectal temperature of ksr2$^{-/-}$ mice suggested that ksr2 might contribute to regulation if body temperature in response to cold exposure. Despite a lower basal temperature, ksr2$^{-/-}$ mice were no different than ksr2$^{+/+}$ mice in their ability to regulate body temperature when exposed to 4° C. for 2 h (FIG. 2f). These data suggest that the ability of the central nervous system to modulate body temperature during cold stress[14] is not impaired by the disruption of ksr2.

Hyperphagia contributes to obesity in other well-characterized models of obesity[16]. However, obese ksr2$^{-/-}$ mice consumed 10% less food than ksr2$^{+/+}$ mice (FIG. 3a). Decreased food consumption was consistent with a sevenfold (females) and 12-fold (males) increase in serum leptin levels in the obese ksr2$^{-/-}$ mice (FIG. 3b). These data suggest that disruption of ksr2 does not disturb leptin-sensitive hypothalamic function inhibiting food intake 7. The orexigenic hypothalamic neuropeptides agouti-related peptide (AgRP) and neuropeptide Y (NPY), whose expression is suppressed by leptin[18], are modestly but not significantly decreased in ksr2$^{-/-}$ mice (FIG. 3c). Similar results were observed when measuring the expression of proopiomelanocortin (POMC)[19] and cocaine- and amphetamine-regulated transcript (CART)[19], which inhibit food intake.

Figure 3F:
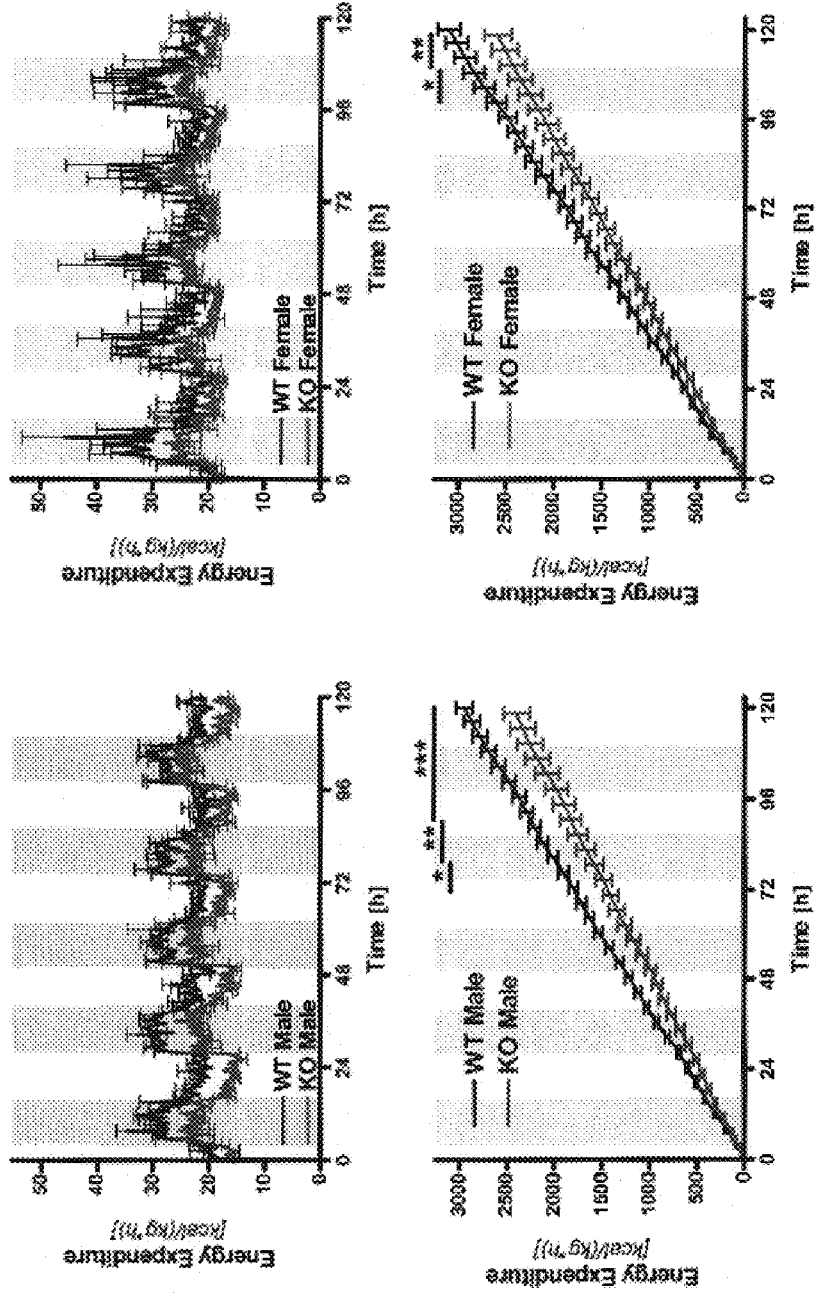
FIG. 3. Behavioral and metabolic characteristics of ksr2$^{-/-}$ mice. Food consumption (a), serum leptin concentrations (b), neuropeptide mRNA expression (c), respiratory quotient (d), cumulative total locomotor activity (e) and cumulative energy expenditure (f) in male and female wild-type and ksr2$^{-/-}$ mice.

During their dark cycle, respiratory quotient (RQ) is suppressed in ksr2$^{-/-}$ mice relative to ksr2$^{+/+}$ mice (FIG. 3d), indicating a preference for the metabolism of fatty acids during active periods. Despite their obesity, locomotor activity is also increased in ksr2$^{-/-}$ mice (FIG. 3e). The consequence of these physiological responses to the disruption of ksr2 would decrease energy storage as fat. However, ksr2$^{-/-}$ mice expend less energy than ksr2$^{+/+}$ mice (FIG. 3f). Thus, despite compensatory responses to their increased adiposity, ksr2$^{-/-}$ mice become obese because they are energy efficient.

Figure 4:
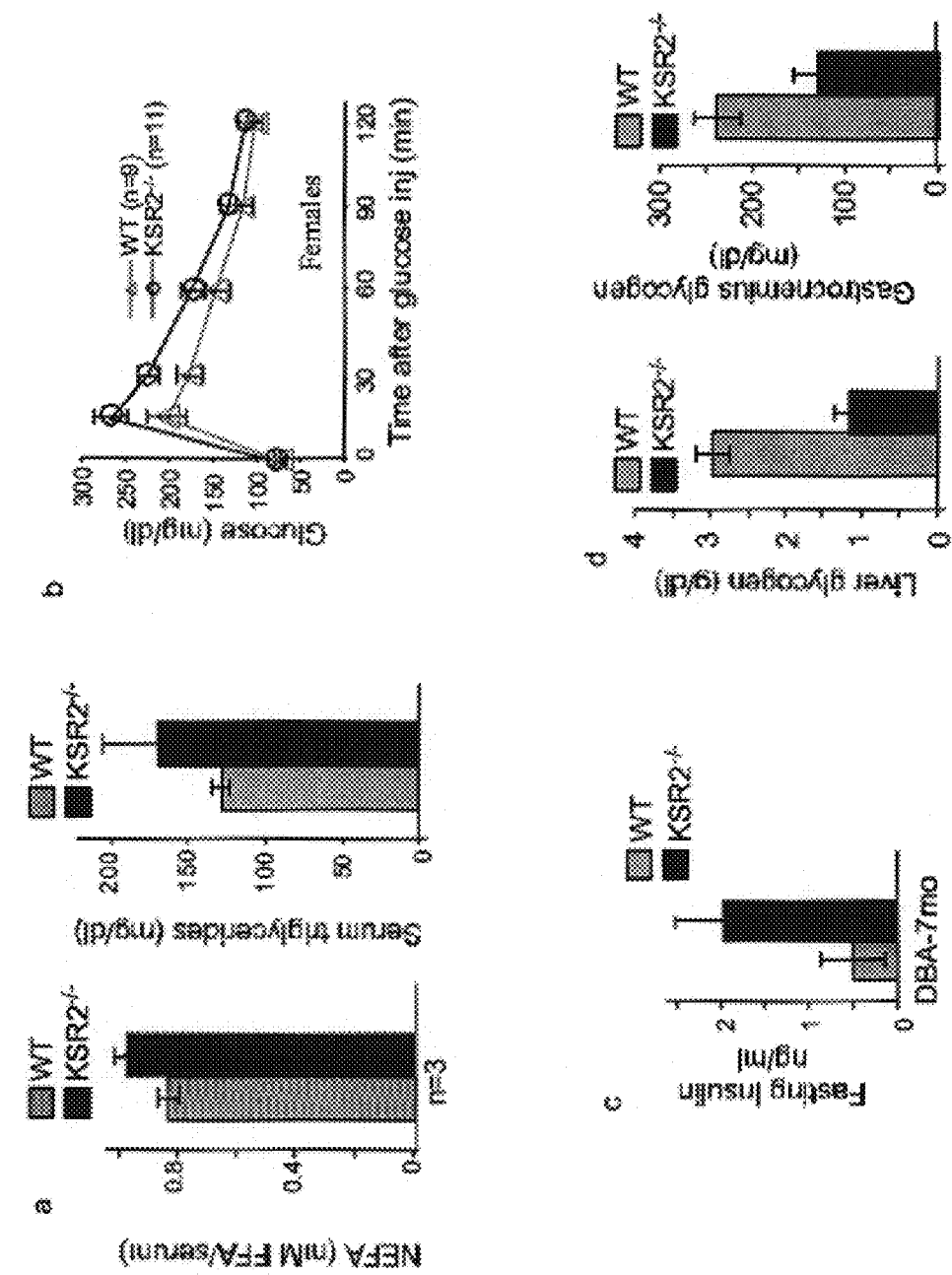
FIG. 4. Lipid, glucose and insulin homeostasis is disrupted in ksr2$^{-/-}$ mice. Serum concentrations of non-esterified free fatty acids (left panel) and triglycerides (right panel) (a), glucose tolerance tests (b), serum insulin (c), and tissue glycogen from liver (left panel) and gastrocnemius (right panel) in wild-type and ksr2$^{-/-}$ mice.
Figure 5:
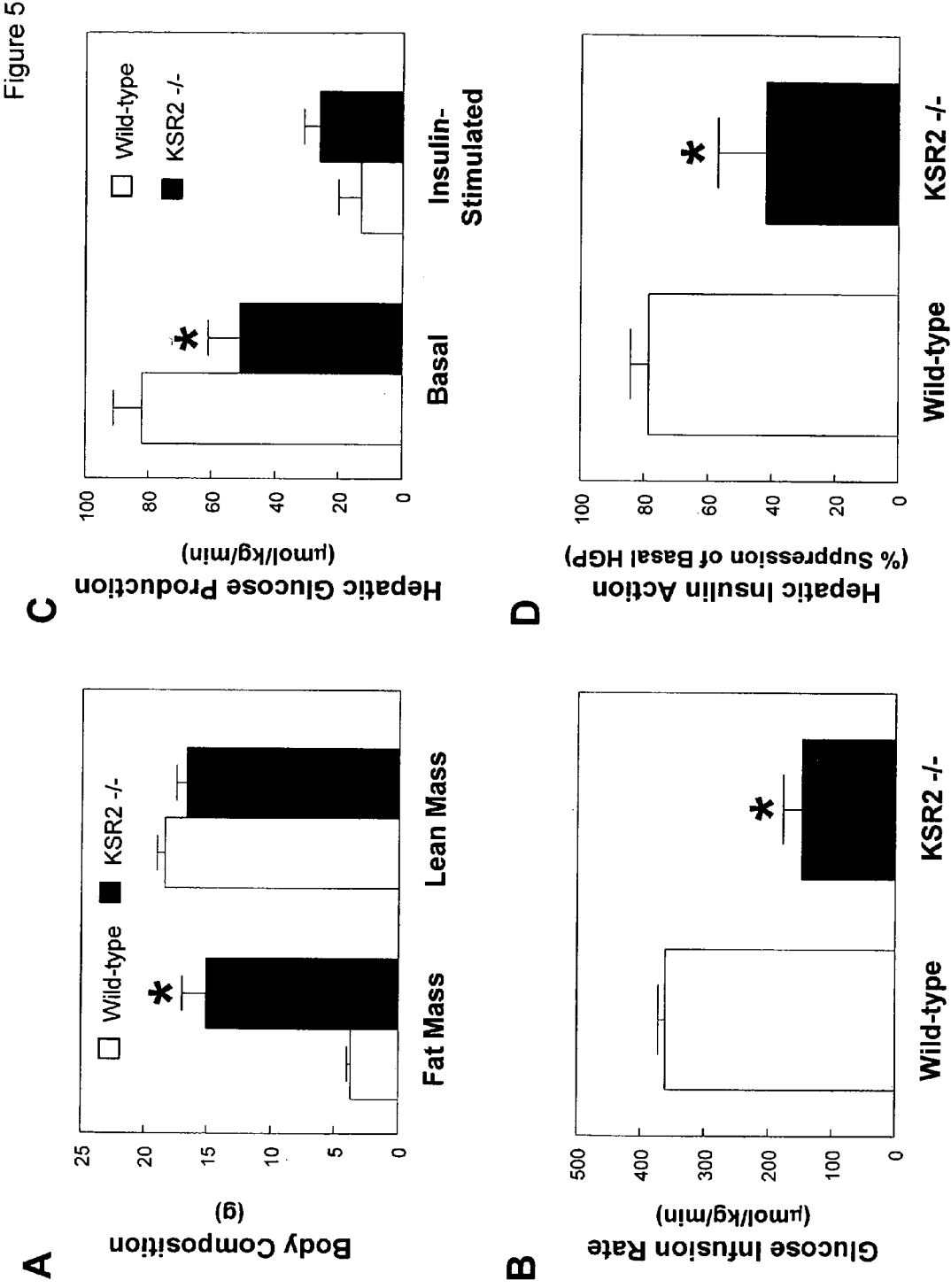
FIG. 5. Body composition and hepatic glucose metabolism in ksr2$^{-/-}$ mice and wild-type littermates. A. Whole body fat and lean mass. B. Steady state glucose infusion rate, obtained from averaged rates of 90 to 120 min of hyperinsulinemic-euglycemic clamps. C. Hepatic glucose production (HGP) during basal and insulin-stimulated (clamp) states. D. Hepatic insulin action reflected as the percent suppression of basal HGP during insulin clamps. Values are means±S.E. for 8~11 experiments. *P<0.05 vs. wild-type mice.
Figure 7:
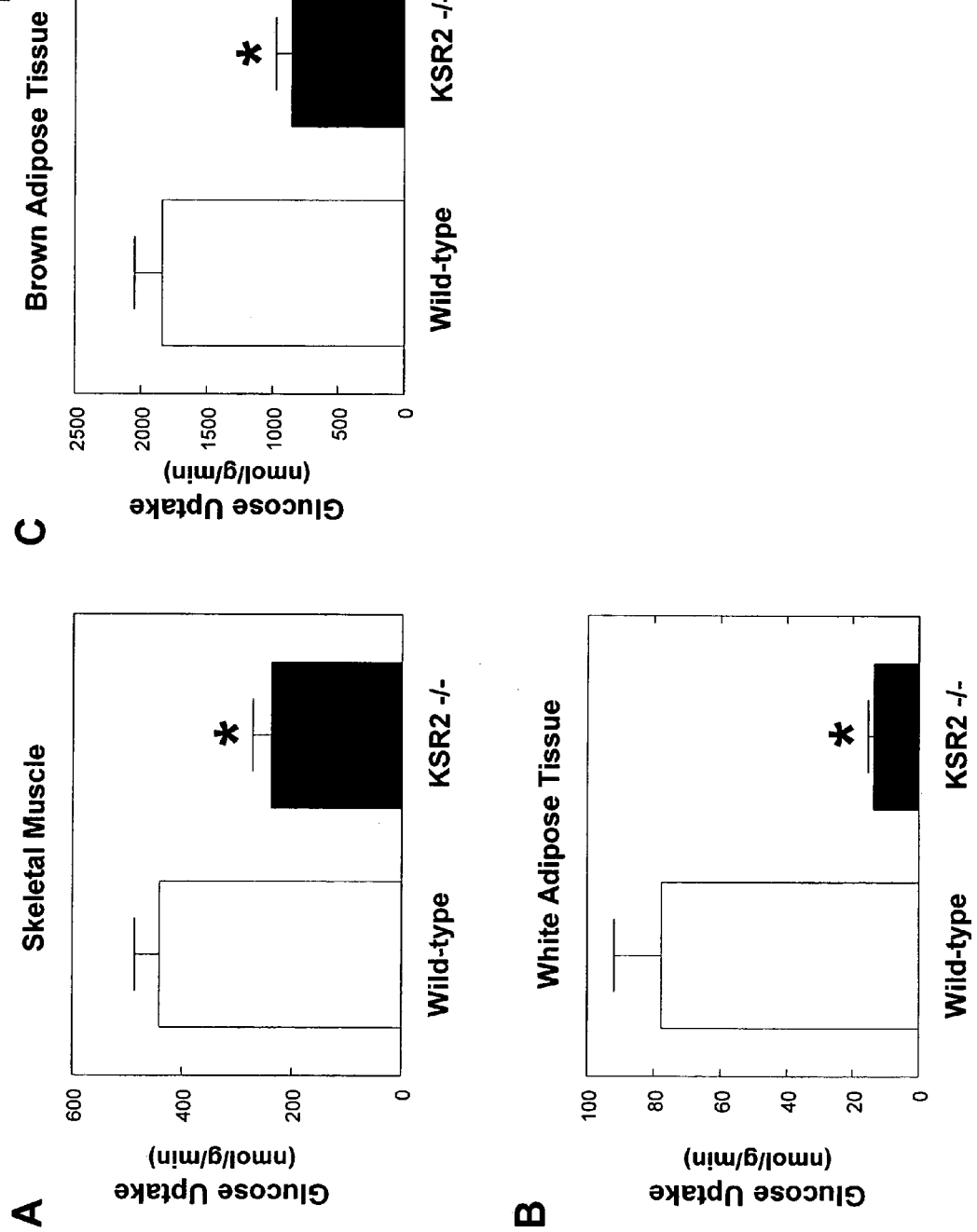
FIG. 7. Organ-specific glucose uptake during clamps in ksr2$^{-/-}$ mice. A. skeletal muscle (gastrocnemius). B. white adipose tissue (epidydimal). C. brown adipose tissue (intrascapular). Values are means±S.E. for 8~11 experiments. *P<0.05 vs. wild-type mice.
Figure 8A:
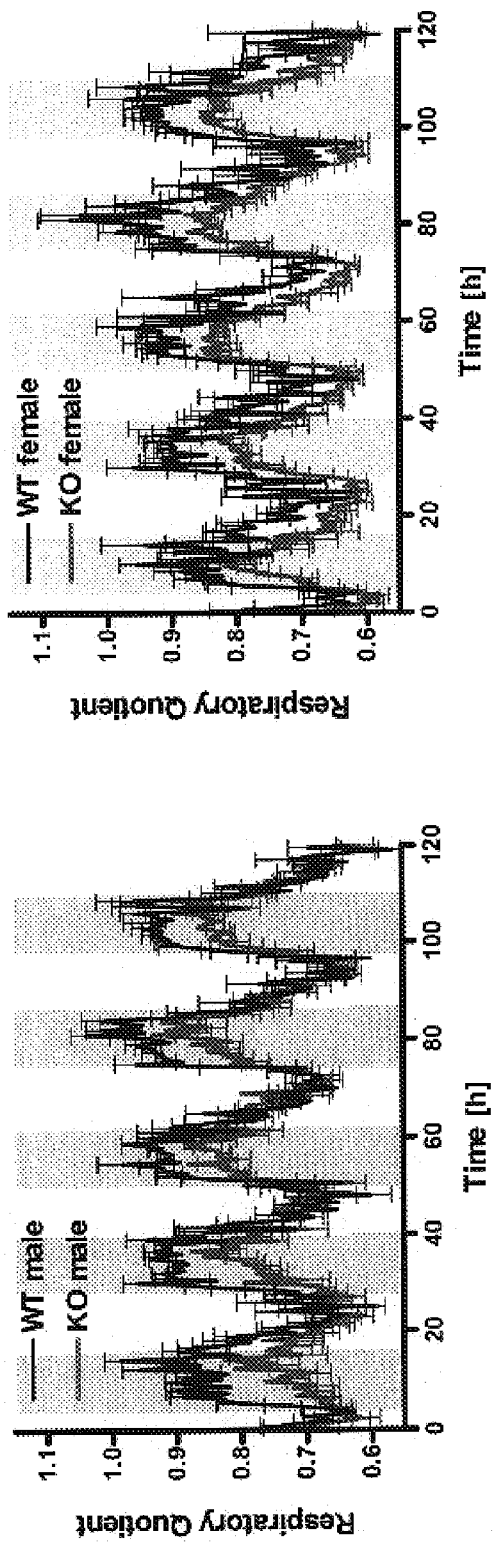
FIG. 8. Additional analysis of metabolic characteristics in ksr2$^{-/-}$ mice. Respiratory quotient (a), ambulatory activity (b) and fine movement (c) analyses in male and female wild-type and ksr2$^{-/-}$ mice.
Figure 8B:
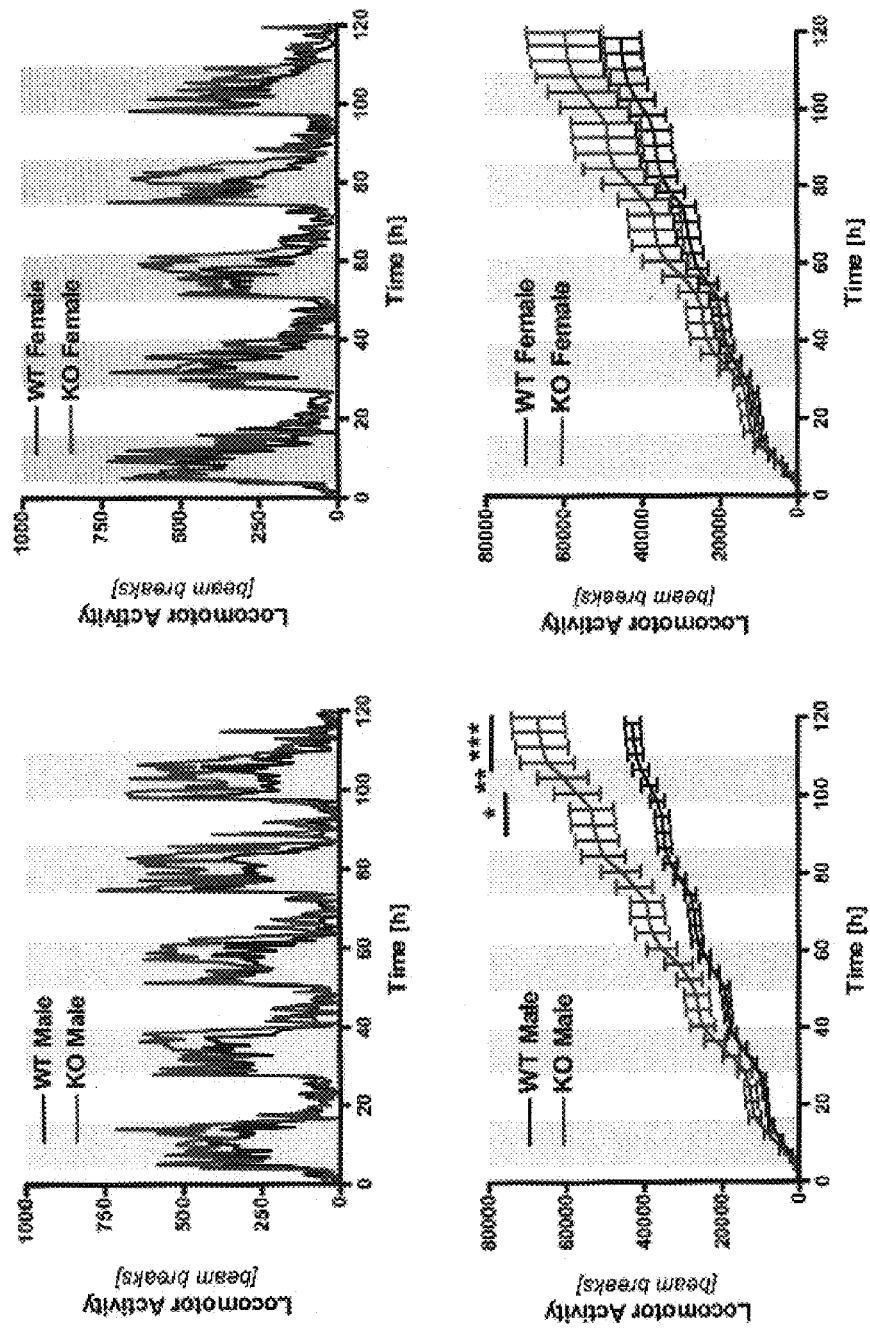
Figure 8C:
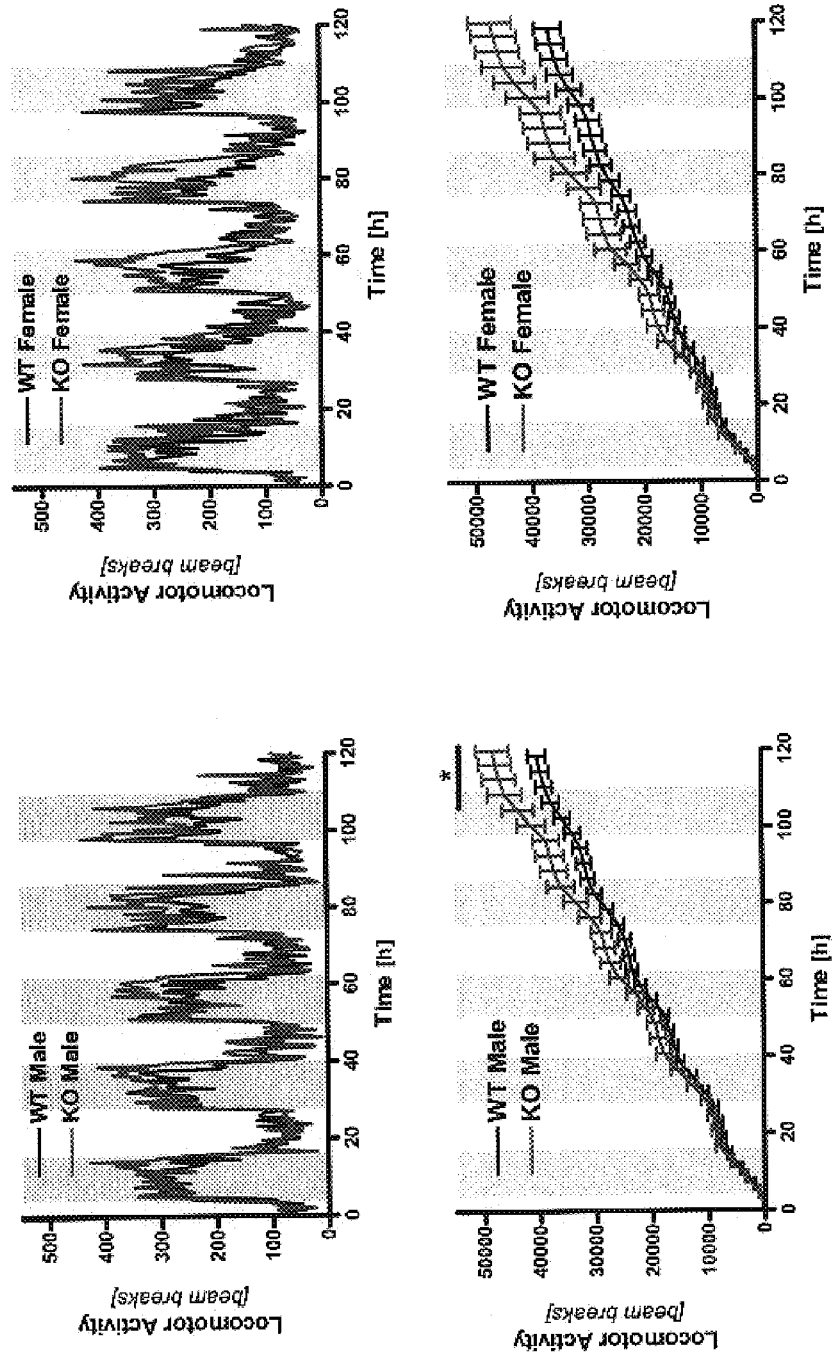
Figure 9A:
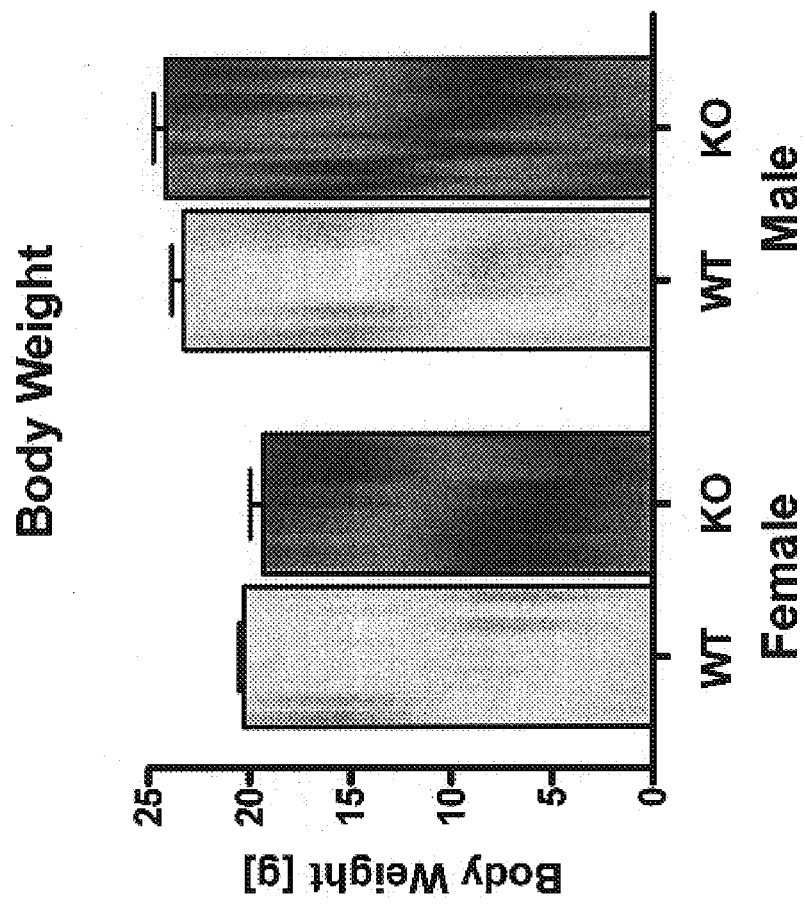
FIG. 9A is a graph depicting the differences in body weight between male and female wildtype and knockout mice.
Figure 9B:
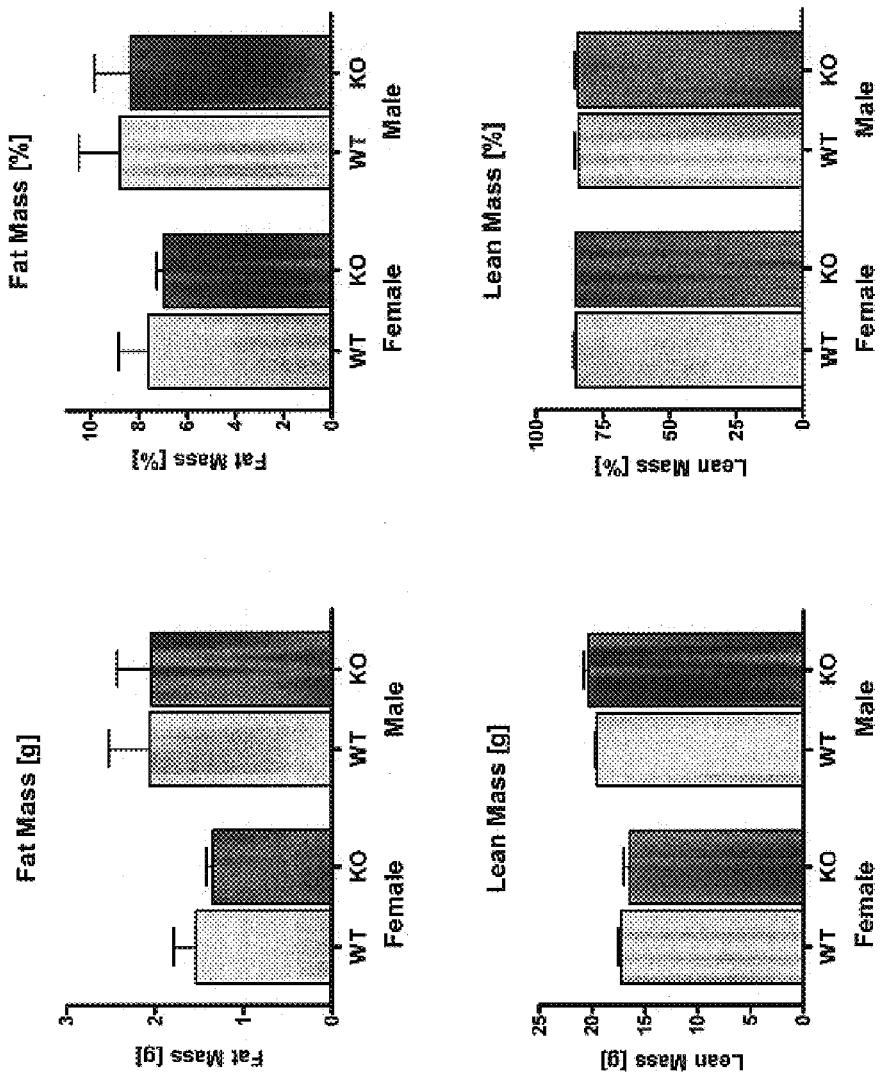
FIG. 9B is a series of graphs showing a comparison of fat and lean body mass in male and female wild type and knock out mice.
Figure 9C:
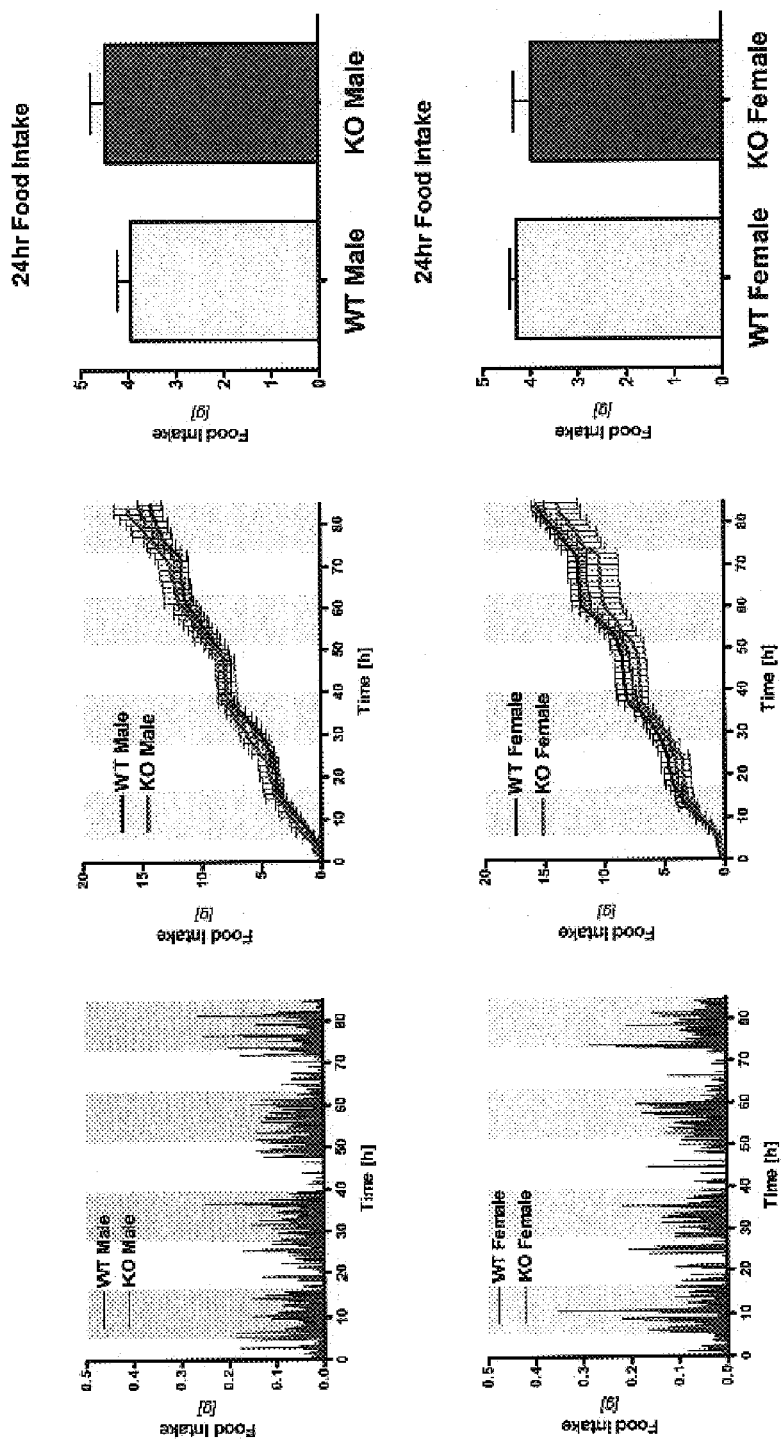
FIG. 9C is a series of graphs depicting food intake in male and female wild type and knock out mice.
Figure 9E:
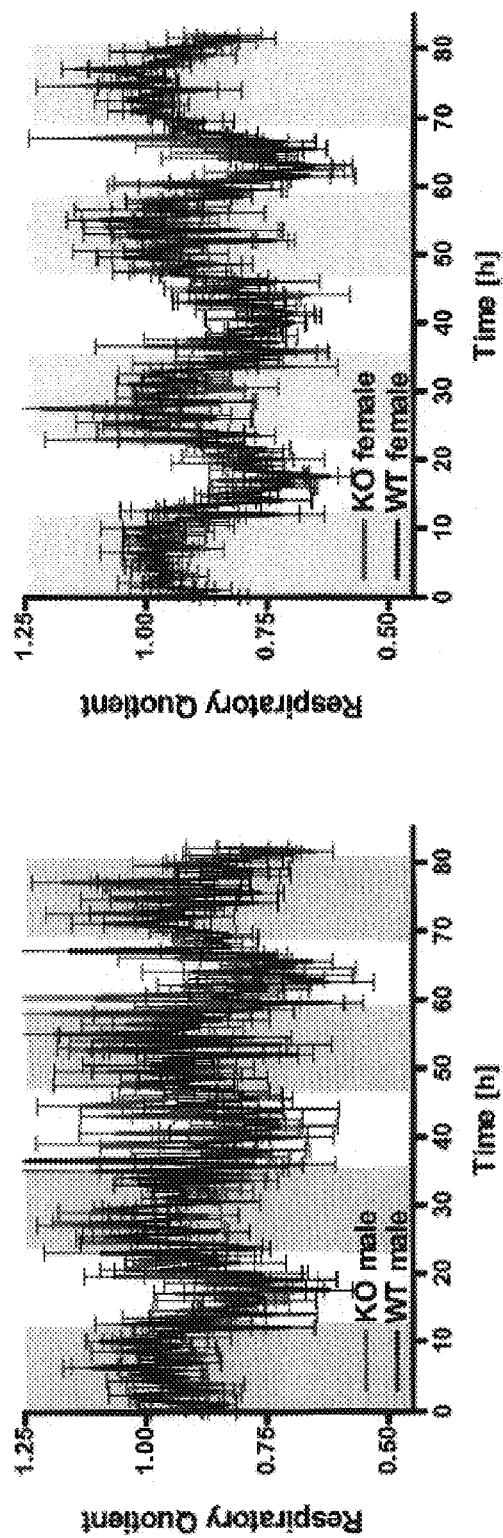
FIG. 9E is a pair of graphs measuring respiratory quotient in male and female wild type and knock out mice.
Figure 10:
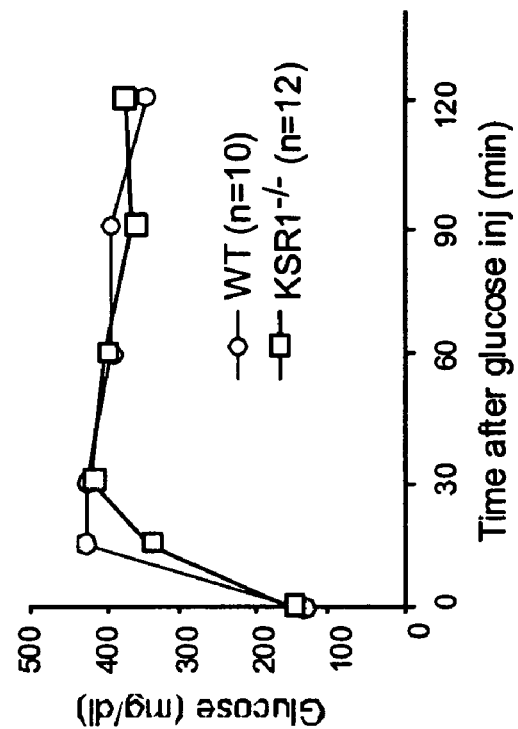
FIG. 10. Glucose tolerance in wild-type and ksr1$^{-/-}$ mice on chow diets containing 4% fat (left panel) and 24% fat (right panel).
Figure 10:
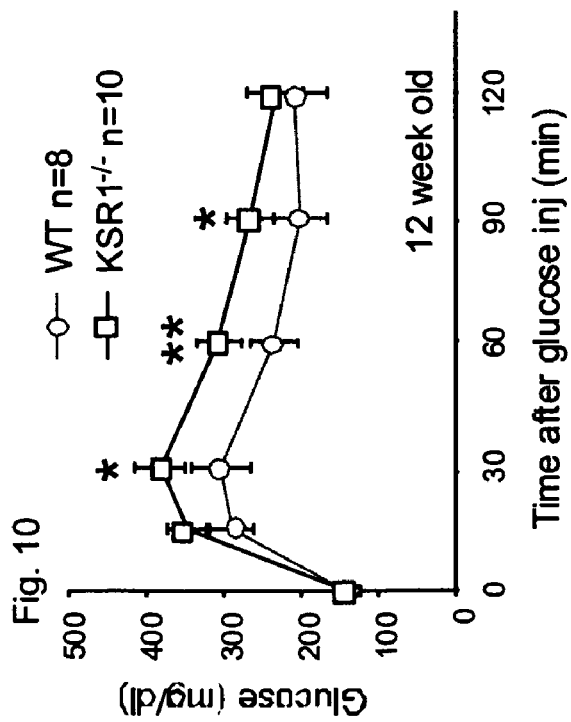

Obesity elevates serum lipids and predisposes rodents and humans to dysregulated glucose homeostasis[20]. ksr2$^{-/-}$ mice show modestly elevated triglycerides and free fatty acids (FIG. 4a).). Glucose tolerance tests showed blunted ability of female ksr2$^{-/-}$ mice to clear a glucose load from their bloodstream (FIG. 4b), and this was associated with elevated fasting insulin levels in ksr2$^{-/-}$ mice (FIG. 4c). To further examine the metabolic effects of ksr2 deletion, we performed a 2-hr hyperinsulinemic-euglycemic clamp in wild-type and ksr2$^{-/-}$ mice. Prior to the clamps, $^1$H-MRS was used to non-invasively measure body composition and confirmed significantly elevated whole body fat mass in ksr2$^{-/-}$ mice with normal whole body lean mass (FIG. 5A). Since the pattern of metabolic effects was comparable in male and female ksr2$^{-/-}$ mice, the following results indicate combined clamp data of male and female mice. During the clamps, the rates of glucose infused to maintain euglycemia (~6 mM) were reduced by ~60% in ksr2$^{-/-}$ mice as compared to wild-type mice, suggesting that obese ksr2$^{-/-}$ mice are insulin resistant (FIG. 5B). Basal hepatic glucose production (HGP) was significantly decreased in ksr2$^{-/-}$ mice, and hepatic insulin action, as reflected by insulin-mediated percent suppression of basal HGP, was reduced by more than 30% in ksr2$^{-/-}$ mice (FIGS. 5C and 5D). Insulin-stimulated whole body glucose turnover was markedly decreased in ksr2$^{-/-}$ mice, indicating that ksr2 deletion caused insulin resistance in liver and peripheral tissues (FIG. 6A). Whole body glycolysis and glycogen plus lipid synthesis were similarly reduced in ksr2$^{-/-}$ mice (FIGS. 6B and 6C). These data are consistent with the markedly reduced glycogen content in the livers and glycolytic muscle of ksr2$^{-/-}$ mice (FIG. 4d). Organ-specific glucose uptake was measured using non-metabolizable glucose analog, 2-deoxyglucose, during clamps. Insulin-stimulated glucose uptake in skeletal muscle (gastrocnemius) was reduced by ~50% in ksr2$^{-/-}$ mice (FIG. 7A). Glucose uptake into white (epididymal) and brown (intrascapular) adipose tissues were also reduced by 50~80% in ksr2$^{-/-}$ mice (FIGS. 7B and 7C). Thus, the clamp data reveal that disruption of ksr2 caused severe insulin resistance in liver, skeletal muscle and adipose tissue that may be partly due to increased adiposity.

ksr1 is a related gene whose protein product functions as a scaffold for the Raf/MEK/ERK signaling cassette, facilitating the activation of Raf and MEK[7,10,21-25] Although ksr1$^{-/-}$ mice are lean and do not display metabolic characteristics observed in ksr2$^{-/-}$ mice (FIGS. 9 and 10), they have hypertrophic adipocytes[5]. Adipocyte hypertrophy has been implicated in altered glucose homeostasis[26,27]. Glucose tolerance was not altered by disruption of ksr1 in the DBA/1 LacJ strain (not shown). However, glucose intolerance was observed in ksr1$^{-/-}$ mice on the C57/BL6J background (FIG. 10). A diet with elevated fat did not significantly enhance the glucose intolerance of ksr1$^{-/-}$ mice on the C57/BL6J background. However, elevated fat in the diet of wild-type C57/BL6J mice caused glucose intolerance that was indistinguishable from ksr1$^{-/-}$ C57/BL6J mice (FIG. 10). These data indicate that disruption of ksr1 plays a previously undetected role in the regulation of glucose metabolism.

The results presented herein demonstrate that disruption of ksr2 causes obesity through a more efficient expenditure of energy. A reduced rate of energy expenditure is a risk factor for weight gain in humans[13]. These observations reveal ksr2$^{-/-}$ mice to be a unique model of obesity with potential relevance to human disease. Moreover, both ksr1 and ksr2 appear to affect glucose homeostasis in mice. Analysis of ksr2 and is effectors may provide important insight into novel mechanisms regulating physiological control of energy storage and expenditure with implications for insulin resistance and diabetes. That molecular scaffolds regulating the activation of Raf, MEK and ERK can have a profound effect on fat accumulation suggests that this MAP kinase may have previously unappreciated roles in the regulation of energy balance.

REFERENCES

1. Haslam, D. W. & James, W. P. Obesity. *Lancet* 366, 1197-209 (2005).
2. Clement, K. Genetics of human obesity. *Proc Nutr Soc* 64, 133-42 (2005).
3. Farooqi, I. S. & O'Rahilly, S. Monogenic obesity in humans. *Annu Rev Med* 56, 443-58 (2005).
4. Channavajhala, P. L. et al. Identification of a novel human kinase supporter of Ras (hKSR-2) that functions as a negative regulator of Cot (Tp12) signaling. *J Biol Chem* 278, 47089-97 (2003).
5. Kortum, R. L. et al. The molecular scaffold kinase suppressor of Ras 1 (KSR1) regulates adipogenesis. *Mol Cell Biol* 25, 7592-604 (2005).
6. Kortum, R. L. et al. The molecular scaffold kinase suppressor of Ras 1 is a modifier of RasV12-induced and replicative senescence. *Mol Cell Biol* 26, 2202-14 (2006).
7. Kortum, R. L. & Lewis, R. E. The molecular scaffold KSR1 regulates the proliferative and oncogenic potential of cells. *Mol Cell Biol* 24, 4407-16 (2004).
8. Ohmachi, M. et al. *C. elegans* ksr-1 and ksr-2 have both unique and redundant functions and are required for MPK-1 ERK phosphorylation. *Curr Biol* 12, 427-33 (2002).
9. Muller, J., Cacace, A. M., Lyons, W. E., McGill, C. B. & Morrison, D. K. Identification of B-KSR1, a novel brain-specific isoform of KSR1 that functions in neuronal signaling. *Mol Cell Biol* 20, 5529-39 (2000).
10. Nguyen, A. et al. Kinase suppressor of Ras (KSR) is a scaffold which facilitates mitogen-activated protein kinase activation in vivo. *Mol Cell Biol* 22, 3035-45 (2002).
11. Douziech, M., Sahmi, M., Laberge, G. & Therrien, M. A KSR/CNK complex mediated by HYP, a novel SAM domain-containing protein, regulates RAS-dependent RAF activation in *Drosophila*. *Genes Dev* 20, 807-19 (2006).
12. Lozano, J. et al. Deficiency of kinase suppressor of Ras1 prevents oncogenic ras signaling in mice. *Cancer Res* 63, 4232-8 (2003).
13. Ravussin, E. et al. Reduced rate of energy expenditure as a risk factor for body-weight gain. *N Engl J Med* 318, 467-72 (1988).
14. Lowell, B. B. & Spiegelman, B. M. Towards a molecular understanding of adaptive thermogenesis. *Nature* 404, 652-60 (2000).
15. Mousel, M. R., Stroup, W. W. & Nielsen, M. K. Locomotor activity, core body temperature, and circadian rhythms in mice selected for high or low heat loss. *J Anim Sci* 79, 861-8 (2001).
16. Bray, G. A. & York, D. A. Hypothalamic and genetic obesity in experimental animals: an autonomic and endocrine hypothesis. *Physiol Rev* 59, 719-809 (1979).
17. Halaas, J. L. et al. Weight-reducing effects of the plasma protein encoded by the obese gene. *Science* 269, 543-6 (1995).
18. Schwartz, M. W., Woods, S. C., Porte, D., Jr., Seeley, R. J. & Baskin, D. G. Central nervous system control of food intake. *Nature* 404, 661-71 (2000).
19. Kristensen, P. et al. Hypothalamic CART is a new anorectic peptide regulated by leptin. *Nature* 393, 72-6 (1998).
20. Lazar, M. A. How obesity causes diabetes: not a tall tale. *Science* 307, 373-5 (2005).
21. Muller, J., Ory, S., Copeland, T., Piwnica-Worms, H. & Morrison, D. K. C-TAK1 regulates Ras signaling by phosphorylating the MAPK scaffold, KSR1. *Mol Cell* 8, 983-93 (2001).
22. Therrien, M. et al. KSR, a novel protein kinase required for RAS signal transduction. *Cell* 83, 879-88 (1995).
23. Kornfeld, K., Hom, D. B. & Horvitz, H. R. The ksr-1 gene encodes a novel protein kinase involved in Ras-mediated signaling in *C. elegans*. *Cell* 83, 903-13 (1995).
24. Sundaram, M. & Han, M. The *C. elegans* ksr-1 gene encodes a novel Raf-related kinase involved in Ras-mediated signal transduction. *Cell* 83, 889-901 (1995).
25. Therrien, M., Michaud, N. R., Rubin, G. M. & Morrison, D. K. KSR modulates signal propagation within the MAPK cascade. *Genes Dev* 10, 2684-95 (1996).
26. Le Lay, S. et al. Cholesterol, a cell size-dependent signal that regulates glucose metabolism and gene expression in adipocytes. *J Biol Chem* 276, 16904-10 (2001).
27. Olefsky, J. M. Mechanisms of decreased insulin responsiveness of large adipocytes. *Endocrinology* 100, 1169-77 (1977).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for screening an agent for the ability to modulate energy expenditure, comprising:
   a) administering the agent to a transgenic mouse whose genome comprises a homozygous disruption of the endogenous KSR-2 gene, wherein no KSR-2 protein is expressed and said mouse exhibits a phenotype comprising increased obesity and reduced energy expenditure by 20-24 weeks of age;
   b) measuring at least one energy expenditure parameter in the mouse of step a);
   c) comparing the measurement obtained in step b) to that a transgenic littermate not administered the agent, thereby identifying agents which modulate energy metabolism in the treated mouse relative to the non-treated control mouse.

2. The method according to claim 1, wherein said parameter is selected from the group consisting of weight, body fat composition, adipose cell mass, adipose cell size, food intake, respiratory quotient, energy expenditure, glucose tolerance, locomotor activity and rectal temperature.

3. The method of claim 1, wherein said agent inhibits energy expenditure in said treated mouse.

4. The method of claim 1, wherein said agent augments energy expenditure in said treated mouse.

5. The method of claim 1, further comprising isolating cells from said mouse and exposing said cells to said agent in vitro.

6. The method of claim 1, wherein said parameter is locomotor activity which is assessed using an infrared beam break assay.

7. The method of claim 1, wherein said parameter is energy expenditure which is assessed via measurement of body heat elaborated via indirect calorimetry.

8. The method of claim 1, wherein said parameter is respiratory quotient which is assessed via determining the ratio of carbon dioxide output to oxygen uptake.

9. The method of claim 1, wherein said parameter is glucose tolerance.

10. The method of claim 1, wherein said parameter is adipose cell mass.

11. The method of claim 1, wherein said parameter is adipose cell size.

12. The method of claim 1, wherein said parameter is body fat composition.

* * * * *